US006441131B1

(12) United States Patent
Hayashi et al.

(10) Patent No.: US 6,441,131 B1

(45) Date of Patent: Aug. 27, 2002

(54) PEPTIDES, METHOD FOR ASSAYING HUMAN PEPSINOGEN II OR HUMAN PEPSIN II, AND ASSAYING KIT

(75) Inventors: Akio Hayashi; Masayoshi Matsuo, both of Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/581,944

(22) PCT Filed: Dec. 21, 1998

(86) PCT No.: PCT/JP98/05780

§ 371 (c)(1),
(2), (4) Date: Jun. 20, 2000

(87) PCT Pub. No.: WO99/32511

PCT Pub. Date: Jan. 7, 1999

(30) Foreign Application Priority Data

Dec. 22, 1997 (JP) .............................................. 9-364796
Jul. 13, 1998 (JP) .............................................. 10-213513

(51) Int. Cl.$^7$ ........................ A61K 38/00; C07K 14/00; C12Q 1/00; A01N 61/00

(52) U.S. Cl. ........................ 530/300; 530/305; 530/332; 530/333; 435/4; 514/1

(58) Field of Search .............................. 435/4; 530/300, 530/305, 332, 333; 514/1

(56) References Cited

U.S. PATENT DOCUMENTS 5,416,197 A 5/1995 Raper et al. ............. 530/387.9
5,879,897 A 3/1999 Koufman ..................... 435/7.4

FOREIGN PATENT DOCUMENTS

WO WO 95/07706 3/1995
WO WO 98/22504 5/1998
WO 98/25952 6/1998 ............ C07K/7/06
WO WO 99/06439 2/1999
WO WO 99/11796 3/1999
WO WO 00/12708 3/2000

OTHER PUBLICATIONS

Miyazawa, Toshifumi et al., "Enzymatic synthesis of peptides containing non–protein amino acids. II", Peptide Chemistry, 1993, p. 93–96.

Filippova, Irina Yu et al., "Flurogenic Peptide Substrates for Assay of Aspartyl Proteinases", Analytical Biochemistry, vol. 234, 1996, 113–118.

Hillier et al, *Genome Res.,* 6(9):807–828 (1996) (XP002170467).

(List continued on next page.)

*Primary Examiner*—Jezia Riley
(74) *Attorney, Agent, or Firm*—Sughrue Mion, PLLC

(57) ABSTRACT

A peptide of the formula (I)

(I)

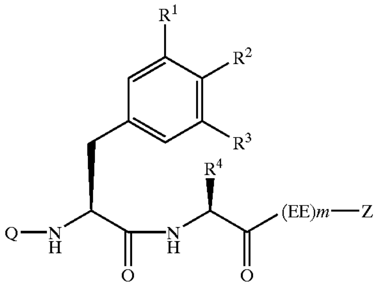

(wherein each symbol is as defined in the description.) or an acid addition salt thereof.

A compound of the formula (I) is a specific substrate for human pepsin II, so it can be used for assaying human pepsin II or human pepsinogen II and it is useful for diagnosis of gastric diseases such as gastric cancer and gastric ulcer.

11 Claims, 4 Drawing Sheets

OTHER PUBLICATIONS

Hillier et al, *Genome Res.,* 6(9):807–828 (1996) (XP002170468).

Luo et al, *Cell,* 75:217–227 (1993).

Adams et al, *Nature Genetics,* 4:373–380 (1993).

Kolodkin et al, *Cell,* 75:1389–1399 (1993).

Shirozu et al, *Genomics,* 37:273–280 (1996).

Bakker et al, *J. of Biol. Chem.,* 272(47):29942–29946 (1997).

Hillier et al, "zx53f01.rl Soares Fetal Liver Spleen 1 NFLS S1 Human cDNA clone Image:446233" (1997).

Hillier et al, "ym48a04.41 Soares Infant Brain 1NIB Human cDNA Image:51336" (1995).

Pirozzi et al, *J. Immunol.,* 155:5811–5818 (1995).

Stewart et al, *J. Immunol.,* 156:1221–1228 (1996).

Auffray et al, "Human Partial cDNA Sequence, Clone 66F05" (1995).

Marra et al, "mm66g05.rl Stratagene Mouse Macrophage (#937306) Mus Musculus cDNA Clone Image:533432" (1996).

Mahler et al., *Biological Chem.,*$2^{nd}$Ed., Harper & Row, Publishers, New York, p. 117 (1971).

Tang, *Meth. in Enzymology,*19:406–421 (1970).

Lehninger Biochemistry Copyright@1975 by Worth Publishers, Inc., Chapter 21.

Grabner et al, Scand. J. *Gastroenterol.,* 12(7):865–868 (1977 (recd) 1978)) abstract only.

Jablonowski et al, *Med. Weter.,* 47(9):423–424(1991) abstract only.

Roth et al, *Clinica Chimica Acta,* 135:65–71 (1983).

Vercaigne–Marko et al, *Biol. Chem.,* 368:37–45 (1987).

Lysogorskaya et al. Bioorganicheskaya Khimya, 9(4): 470–477 (1983) Abstract only.

Vance et al. Biochemistry, 36 (43): 13232–13240 (1997) Abstract only.

SEQUENCE LISTING

<160> NUMBER OF SEQ ID NOS: 92

<210> SEQ ID NO 1
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 1

Pro Leu Ser Glu Xaa Xaa
1 5

<210> SEQ ID NO 2
<211> LENGTH: 4
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (3)..(3)
<223> OTHER INFORMATION: 4-Iodo-Phenyl Ala
<220> FEATURE:
<221> NAME/KEY: MISC_FEATURE
<222> LOCATION: (4)..(4)
<223> OTHER INFORMATION: Gly which binds to p-nitroaniline

<400> SEQUENCE: 2

Leu Ser Xaa Xaa
1

<210> SEQ ID NO 3
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Gly which binds to p-nitroaniline

<400> SEQUENCE: 3

Pro Gln Gln Ala Xaa Xaa
1 5

<210> SEQ ID NO 4
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 4-Iodo-Phenyl Ala
<220> FEATURE:

-continued

<221> NAME/KEY: MISC_FEATURE
<222> LOCATION: (6)..(6)
<223> OTHER INFORMATION: Gly which binds to p-nitroaniline

<400> SEQUENCE: 4

Pro Gln Gln Ala Xaa Xaa
1 5

<210> SEQ ID NO 5
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 4-Chloro-Phenyl Ala
<220> FEATURE:
<221> NAME/KEY: MISC_FEATURE
<222> LOCATION: (6)..(6)
<223> OTHER INFORMATION: Gly which binds to p-nitroaniline

<400> SEQUENCE: 5

Pro Gln Gln Ala Xaa Xaa
1 5

<210> SEQ ID NO 6
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 6

Pro Gln Gln Ala Xaa Xaa
1 5

<210> SEQ ID NO 7
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 4-Iodo-Phenyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 7

Pro Gln Gln Ala Xaa Xaa
1 5

<210> SEQ ID NO 8
<211> LENGTH: 6
<212> TYPE: PRT
<213> ORGANISM: Artificial Sequence
<220> FEATURE:
<223> OTHER INFORMATION: substrate for human pepsin II or pepsinogen II -continued

```
<220> FEATURE:
<221> NAME/KEY: MISC_FEATURE
<222> LOCATION: (5)..(5)
<223> OTHER INFORMATION: 4-Chloro-Phenyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 8

Pro Gln Gln Ala Xaa Xaa
1               5


<210> SEQ ID NO 9
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: 2Abu which binds to p-nitroaniline

<400> SEQUENCE: 9

Pro Gln Gln Ala Xaa Xaa
1               5


<210> SEQ ID NO 10
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 4-Iodo-Phenyl Ala
<220> FEATURE:
<221> NAME/KEY: MISC_FEATURE
<222> LOCATION: (6)..(6)
<223> OTHER INFORMATION: 2Abu which binds to p-nitroaniline

<400> SEQUENCE: 10

Pro Gln Gln Ala Xaa Xaa
1               5


<210> SEQ ID NO 11
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 4-Chloro-Phenyl Ala
<220> FEATURE:
<221> NAME/KEY: MISC_FEATURE
<222> LOCATION: (6)..(6)
<223> OTHER INFORMATION: 2Abu which binds to p-nitroaniline

<400> SEQUENCE: 11

Pro Gln Gln Ala Xaa Xaa
1               5
```

-continued

<210> SEQ ID NO 12
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Nva which binds to p-nitroaniline

<400> SEQUENCE: 12

Pro Gln Gln Ala Xaa Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 4-Iodo-Phenyl Ala
<220> FEATURE:
<221> NAME/KEY: MISC_FEATURE
<222> LOCATION: (6)..(6)
<223> OTHER INFORMATION: Nva which binds to p-nitroaniline

<400> SEQUENCE: 13

Pro Gln Gln Ala Xaa Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 4-Chloro-Phenyl Ala
<220> FEATURE:
<221> NAME/KEY: MISC_FEATURE
<222> LOCATION: (6)..(6)
<223> OTHER INFORMATION: Nva which binds to p-nitroaniline

<400> SEQUENCE: 14

Pro Gln Gln Ala Xaa Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: 4-Iodo-Phenyl Ala
<220> FEATURE:
<221> NAME/KEY: MISC_FEATURE -continued
<222> LOCATION: (7)..(7)
<223> OTHER INFORMATION: Ala which binds to p-nitroaniline

<400> SEQUENCE: 15

Lys Pro Gln Gln Ala Xaa Xaa
1               5

<210> SEQ ID NO 16
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (6)..(6)
<223> OTHER INFORMATION: 4-Iodo-Phenyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 16

Leu Pro Gln Gln Ala Xaa Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (6)..(6)
<223> OTHER INFORMATION: 4-Iodo-Phenyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 17

Asn Pro Gln Gln Ala Xaa Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (6)..(6)
<223> OTHER INFORMATION: 4-Iodo-Phenyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 18

Gln Pro Gln Gln Ala Xaa Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:

-continued

<221> NAME/KEY: MISC_FEATURE
<222> LOCATION: (6)..(6)
<223> OTHER INFORMATION: 4-Iodo-Phenyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 19

Ala Pro Gln Gln Ala Xaa Xaa
1               5

<210> SEQ ID NO 20
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (6)..(6)
<223> OTHER INFORMATION: 4-Iodo-Phenyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 20

Val Pro Gln Gln Ala Xaa Xaa
1               5

<210> SEQ ID NO 21
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (6)..(6)
<223> OTHER INFORMATION: 4-Iodo-Phenyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 21

Gly Pro Gln Gln Ala Xaa Xaa
1               5

<210> SEQ ID NO 22
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (6)..(6)
<223> OTHER INFORMATION: 4-Iodo-Phenyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 22

Phe Pro Gln Gln Ala Xaa Xaa
1               5

<210> SEQ ID NO 23
<211> LENGTH: 6

-continued

<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 23

Pro Gln Gln Asn Xaa Xaa
1               5

<210> SEQ ID NO 24
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 24

Pro Gln Gln Gln Xaa Xaa
1               5

<210> SEQ ID NO 25
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 25

Pro Gln Gln Gly Xaa Xaa
1               5

<210> SEQ ID NO 26
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline -continued

<400> SEQUENCE: 26

Pro Gln Gln Met Xaa Xaa
1 5

<210> SEQ ID NO 27
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 27

Pro Gln Gln Ser Xaa Xaa
1 5

<210> SEQ ID NO 28
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 28

Pro Gln Gln Asp Xaa Xaa
1 5

<210> SEQ ID NO 29
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 29

Pro Gln Gln Glu Xaa Xaa
1 5

<210> SEQ ID NO 30
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala -continued
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 30

Pro Gln Asn Glu Xaa Xaa
1 5

<210> SEQ ID NO 31
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 31

Pro Gln Ala Glu Xaa Xaa
1 5

<210> SEQ ID NO 32
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 32

Pro Gln Gly Glu Xaa Xaa
1 5

<210> SEQ ID NO 33
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 33

Pro Gln Leu Glu Xaa Xaa
1 5

<210> SEQ ID NO 34
<211> LENGTH: 6
<212> TYPE: PRT
<213> ORGANISM: Artificial Sequence
<220> FEATURE:

-continued

<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 34

Pro Gln Glu Glu Xaa Xaa
1 5

<210> SEQ ID NO 35
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 35

Pro Gln Asp Glu Xaa Xaa
1 5

<210> SEQ ID NO 36
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 36

Pro Gln Ser Glu Xaa Xaa
1 5

<210> SEQ ID NO 37
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 37

Pro Asn Ser Glu Xaa Xaa
1 5

-continued

<210> SEQ ID NO 38
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 38

Pro Ala Ser Glu Xaa Xaa
1               5

<210> SEQ ID NO 39
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 39

Pro Val Ser Glu Xaa Xaa
1               5

<210> SEQ ID NO 40
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 40

Pro Met Ser Glu Xaa Xaa
1               5

<210> SEQ ID NO 41
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline -continued

<400> SEQUENCE: 41

Pro Ile Ser Glu Xaa Xaa
1 5

<210> SEQ ID NO 42
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 42

Pro Gly Ser Glu Xaa Xaa
1 5

<210> SEQ ID NO 43
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 43

Pro Glu Ser Glu Xaa Xaa
1 5

<210> SEQ ID NO 44
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 44

Pro Asp Ser Glu Xaa Xaa
1 5

<210> SEQ ID NO 45
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala -continued
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 45

Pro Ser Ser Glu Xaa Xaa
1 5

<210> SEQ ID NO 46
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 46

Pro Thr Ser Glu Xaa Xaa
1 5

<210> SEQ ID NO 47
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 47

Asn Leu Ser Glu Xaa Xaa
1 5

<210> SEQ ID NO 48
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 48

Ala Leu Ser Glu Xaa Xaa
1 5

<210> SEQ ID NO 49
<211> LENGTH: 6
<212> TYPE: PRT
<213> ORGANISM: Artificial Sequence
<220> FEATURE:

-continued

<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 49

Val Leu Ser Glu Xaa Xaa
1               5

<210> SEQ ID NO 50
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 50

Met Leu Ser Glu Xaa Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 51

Ile Leu Ser Glu Xaa Xaa
1               5

<210> SEQ ID NO 52
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 52

Gly Leu Ser Glu Xaa Xaa
1               5

-continued

<210> SEQ ID NO 53
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 53

Leu Leu Ser Glu Xaa Xaa
1 5

<210> SEQ ID NO 54
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 54

Gln Leu Ser Glu Xaa Xaa
1 5

<210> SEQ ID NO 55
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 55

Lys Leu Ser Glu Xaa Xaa
1 5

<210> SEQ ID NO 56
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline -continued

<400> SEQUENCE: 56

Glu Leu Ser Glu Xaa Xaa
1 5

<210> SEQ ID NO 57
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 57

Ser Leu Ser Glu Xaa Xaa
1 5

<210> SEQ ID NO 58
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 58

Thr Leu Ser Glu Xaa Xaa
1 5

<210> SEQ ID NO 59
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 59

Tyr Leu Ser Glu Xaa Xaa
1 5

<210> SEQ ID NO 60
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MOD_RES
<222> LOCATION: (1)..(1)
<223> OTHER INFORMATION: ACETYLATION -continued
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 60

Lys Leu Ser Glu Xaa Xaa
1 5

<210> SEQ ID NO 61
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (6)..(6)
<223> OTHER INFORMATION: 2-naphthyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 61

Pro Asn Leu Ser Glu Xaa Xaa
1 5

<210> SEQ ID NO 62
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: 2-naphthyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 62

Lys Asn Leu Ser Glu Xaa Xaa
1 5

<210> SEQ ID NO 63
<211> LENGTH: 8
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (7)..(7)
<223> OTHER INFORMATION: 2-naphthyl Ala
<220> FEATURE:
<221> NAME/KEY: MISC_FEATURE
<222> LOCATION: (8)..(8)
<223> OTHER INFORMATION: Ala which binds to p-nitroaniline -continued

<400> SEQUENCE: 63

Pro Ser Asn Leu Ser Glu Xaa Xaa
1               5

<210> SEQ ID NO 64
<211> LENGTH: 8
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (7)..(7)
<223> OTHER INFORMATION: 2-naphthyl Ala
<220> FEATURE:
<221> NAME/KEY: MISC_FEATURE
<222> LOCATION: (8)..(8)
<223> OTHER INFORMATION: Ala which binds to p-nitroaniline

<400> SEQUENCE: 64

Pro Asn Asn Leu Ser Glu Xaa Xaa
1               5

<210> SEQ ID NO 65
<211> LENGTH: 8
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (7)..(7)
<223> OTHER INFORMATION: 2-naphthyl Ala
<220> FEATURE:
<221> NAME/KEY: MISC_FEATURE
<222> LOCATION: (8)..(8)
<223> OTHER INFORMATION: Ala which binds to p-nitroaniline

<400> SEQUENCE: 65

Pro Gly Asn Leu Ser Glu Xaa Xaa
1               5

<210> SEQ ID NO 66
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: 2-naphthyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 66

Lys Ala Leu Ser Glu Xaa Xaa
1               5

<210> SEQ ID NO 67
<211> LENGTH: 7
<212> TYPE: PRT
<213> ORGANISM: Artificial Sequence
<220> FEATURE:
<223> OTHER INFORMATION: substrate for human pepsin II or pepsinogen II -continued
<220> FEATURE:
<221> NAME/KEY: MISC_FEATURE
<222> LOCATION: (1)..(1)
<223> OTHER INFORMATION: bAla
<220> FEATURE:
<221> NAME/KEY: MISC_FEATURE
<222> LOCATION: (6)..(6)
<223> OTHER INFORMATION: 2-naphthyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 67

Ala Asn Leu Ser Glu Xaa Xaa
1               5

<210> SEQ ID NO 68
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: MeGly
<220> FEATURE:
<221> NAME/KEY: MISC_FEATURE
<222> LOCATION: (6)..(6)
<223> OTHER INFORMATION: 2-naphthyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 68

Gly Asn Leu Ser Glu Xaa Xaa
1               5

<210> SEQ ID NO 69
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: MeVal
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 69

Val Leu Ser Glu Xaa Xaa
1               5

<210> SEQ ID NO 70
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: N-Methyl-Ala -continued
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 70

Xaa Leu Ser Glu Xaa Xaa
1 5

<210> SEQ ID NO 71
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: MeGly
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 71

Gly Leu Ser Glu Xaa Xaa
1 5

<210> SEQ ID NO 72
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 4-Chloro-Phenyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 72

Pro Leu Ser Glu Xaa Xaa
1 5

<210> SEQ ID NO 73
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 3,4-DichloroPhenyl Ala
<220> FEATURE:
<221> NAME/KEY: MISC_FEATURE
<222> LOCATION: (6)..(6)
<223> OTHER INFORMATION: Ala which binds to p-nitroaniline -continued

<400> SEQUENCE: 73

Pro Leu Ser Glu Xaa Xaa
1 5

<210> SEQ ID NO 74
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (5)..(5)
<223> OTHER INFORMATION: 4-Chloro-Phenyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 74

Val Leu Ser Glu Xaa Xaa
1 5

<210> SEQ ID NO 75
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: D-Ala
<220> FEATURE:
<221> NAME/KEY: MISC_FEATURE
<222> LOCATION: (6)..(6)
<223> OTHER INFORMATION: 2-naphthyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 75

Ala Asn Leu Ser Glu Xaa Xaa
1 5

<210> SEQ ID NO 76
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: D-Ala
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 76

Ala Leu Ser Glu Xaa Xaa
1 5

<210> SEQ ID NO 77
<211> LENGTH: 6

-continued

<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: bAla
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 77

Ala Leu Ser Glu Xaa Xaa
1 5

<210> SEQ ID NO 78
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: 4Abu
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 78

Xaa Leu Ser Glu Xaa Xaa
1 5

<210> SEQ ID NO 79
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (4)..(4)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Leu which binds to p-nitroaniline

<400> SEQUENCE: 79

Leu Ser Glu Xaa Ala Xaa
1 5

<210> SEQ ID NO 80
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (4)..(4)
<223> OTHER INFORMATION: 2-naphthyl Ala -continued
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 80

Leu Ser Glu Xaa Ala Xaa
1 5

<210> SEQ ID NO 81
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (4)..(4)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Gly which binds to p-nitroaniline

<400> SEQUENCE: 81

Leu Ser Glu Xaa Ala Xaa
1 5

<210> SEQ ID NO 82
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: MeGly
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (7)..(7)
<223> OTHER INFORMATION: Ala which binds to p-nitroaniline

<400> SEQUENCE: 82

Gly Leu Ser Glu Xaa Ala Xaa
1 5

<210> SEQ ID NO 83
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: MeGly
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (7)..(7)
<223> OTHER INFORMATION: Gly which binds to p-nitroaniline -continued

<400> SEQUENCE: 83

Gly Leu Ser Glu Xaa Ala Xaa
1 5

<210> SEQ ID NO 84
<211> LENGTH: 7
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: MeGly
<220> FEATURE:
<221> NAME/KEY: MISC_FEATURE
<222> LOCATION: (5)..(5)
<223> OTHER INFORMATION: 2-naphthyl Ala
<220> FEATURE:
<221> NAME/KEY: MISC_FEATURE
<222> LOCATION: (7)..(7)
<223> OTHER INFORMATION: Ala which binds to m-anisidine

<400> SEQUENCE: 84

Gly Leu Ser Glu Xaa Ala Xaa
1 5

<210> SEQ ID NO 85
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: MeGly
<220> FEATURE:
<221> NAME/KEY: MISC_FEATURE
<222> LOCATION: (4)..(4)
<223> OTHER INFORMATION: 2-naphthyl Ala
<220> FEATURE:
<221> NAME/KEY: MISC_FEATURE
<222> LOCATION: (6)..(6)
<223> OTHER INFORMATION: Ala which binds to 3,5-Dichloro-4-hydroxyaniline

<400> SEQUENCE: 85

Gly Ser Gly Xaa Ala Xaa
1 5

<210> SEQ ID NO 86
<211> LENGTH: 8
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (6)..(6)
<223> OTHER INFORMATION: p-nitrophenylalanine

<400> SEQUENCE: 86

Lys Pro Ala Ala Phe Xaa Arg Leu
1 5

<210> SEQ ID NO 87
<211> LENGTH: 8
<212> TYPE: PRT
<213> ORGANISM: Artificial Sequence
<220> FEATURE:

-continued

<223> OTHER INFORMATION: substrate for human pepsin II or pepsinogen II
<220> FEATURE:
<221> NAME/KEY: MISC_FEATURE
<222> LOCATION: (6)..(6)
<223> OTHER INFORMATION: p-nitrophenylalanine

<400> SEQUENCE: 87

Lys Pro Val Val Phe Xaa Arg Leu
1 5

<210> SEQ ID NO 88
<211> LENGTH: 4
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: Pyroglutamic acid, Asp, Glu, Gly or 2-
oxoimidazolidin-1-yl-carbonyl which bind to hydrogen, C3-5
carboxyalkylcarbonyl or C1-5 alkylcarbonyl
<220> FEATURE:
<221> NAME/KEY: MISC_FEATURE
<222> LOCATION: (2)..(2)
<223> OTHER INFORMATION: His, Gly or Pro
<220> FEATURE:
<221> NAME/KEY: MISC_FEATURE
<222> LOCATION: (4)..(4)
<223> OTHER INFORMATION: Phe, Leu, Nle, Met or S-C1-3 Alkyl-Cys which
bind to p-nitroaniline

<400> SEQUENCE: 88

Xaa Xaa Phe Xaa
1

<210> SEQ ID NO 89
<211> LENGTH: 4
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (4)..(4)
<223> OTHER INFORMATION: Phe which binds to p-nitroaniline

<400> SEQUENCE: 89

Xaa His Phe Xaa
1

<210> SEQ ID NO 90
<211> LENGTH: 4
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: Piroglutamic acid
<220> FEATURE:
<221> NAME/KEY: MISC_FEATURE
<222> LOCATION: (4)..(4)
<223> OTHER INFORMATION: Met which binds to p-nitroaniline -continued

<400> SEQUENCE: 90

Xaa His Phe Xaa
1

<210> SEQ ID NO 91
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: N-o-aminobenzoyl-Ala
<220> FEATURE:
<221> NAME/KEY: MISC_FEATURE
<222> LOCATION: (6)..(6)
<223> OTHER INFORMATION: Ala which binds to N-2,4-dinitrophenyl
ethylenediamine

<400> SEQUENCE: 91

Xaa Ala Phe Phe Ala Xaa
1 5

<210> SEQ ID NO 92
<211> LENGTH: 6
<212> TYPE: PRT
<213> ORGANISM: Artificial Sequence
<220> FEATURE:
<223> OTHER INFORMATION: substrate for human pepsin II or pepsinogen II
<220> FEATURE:
<221> NAME/KEY: MISC_FEATURE
<222> LOCATION: (1)..(1)
<223> OTHER INFORMATION: N-o-aminobenzoyl-Ala
<220> FEATURE:
<221> NAME/KEY: MISC_FEATURE
<222> LOCATION: (6)..(6)
<223> OTHER INFORMATION: Ala which binds to p-nitroaniline

<400> SEQUENCE: 92

Xaa Ala Phe Phe Ala Xaa
1 5

PEPTIDES, METHOD FOR ASSAYING HUMAN PEPSINOGEN II OR HUMAN PEPSIN II, AND ASSAYING KIT

FIELD OF THE INVENTION

The present invention relates to a method for assaying human pepsin II or human pepsinogen II in the human body fluid (such as gastric juice, blood, urine etc.) as diagnostic marker of gastric diseases such as gastric cancer, gastric ulcer etc. and a peptide used as a substrate in such a method.

More detailed, the present invention relates to 1) a peptide of the formula (I)

(I)

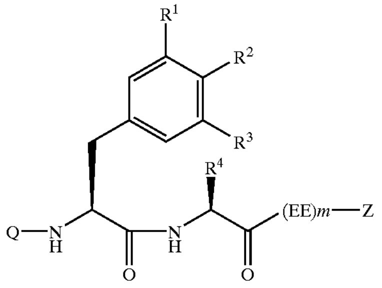

(wherein, Q is $Q^a$—(AA)n— (in which AA is L-amino acid, n is 0 or an integer of 1~15, $Q^a$ is hydrogen, C1~4 alkyl, an amino-protective group, D- or L-amino acid residue or $NH_2$—$(CH_2)$r—CO— (in which r is an integer of 2~7.).), $R^1$ and $R^2$ are (i) hydrogen or halogen or, (ii) $R^1$, $R^2$ and unsaturated bond together form an aromatic carbon ring may be substituted by halogen, $R^3$ is hydrogen or halogen, $R^4$ is hydrogen, C1~3 alkyl or hydroxymethyl, EE is D- or L-amino acid residue, m is 0 or 1, Z is an aniline derivative residue, an aminocoumarine derivative residue or an aminonaphthalene derivative residue, with the proviso that (1) when n is 2 or more, each AA is same or different, and that (2) the compounds wherein all of $R^1$, $R^2$ and $R^3$ is hydrogen are excluded.)

or an acid addition salt thereof and, 2) a method for assaying human pepsinogen II or human pepsin II which is characterized by digesting a peptide of the formula (I) (wherein all the symbols are as defined hereinbefore.) described in the said 1) or an acid addition salt thereof by human pepsin II which is obtained by activation of human pepsinogen II in a sample or human pepsin II in a sample to obtain an amino acid derivative of the formula (II)

(II)

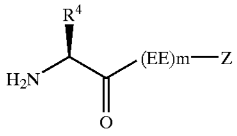

(wherein all the symbols are as defined hereinbefore.), digesting the obtained amino acid derivative by aminopeptidase to obtain an aniline, aminocoumarine or aminonaphthalene derivative of the formula Z—H and then detecting the obtained aniline, aminocoumarine or aminonaphthalene derivative and 3) a kit for assaying human pepsinogen II or human pepsin II which is characterized by comprising a peptide of the formula (I) (wherein all the symbols are as defined hereinbefore.) described in the said 1) or an acid addition salt thereof as a substrate and an aminopeptidase.

BACKGROUND

It is known that the pepsinogen secretion is parallel to gastric acid secretion and that human serum or urine pepsinogen levels are also parallel to gastric pepsinogen secretion. The above pepsinogen exists as pepsinogen in the body fluid such as blood or urine except for gastric juice, on the other hand, it exists as pepsin in gastric juice.

It is said that human blood or urine pepsinogen I level of the patient with atrophic gastritis decreases and that human blood or urine pepsinogen I and pepsinogen II levels increase in case of gastric ulcer (Japanese Patent Application Kokai Hei 7-304800). In addition, it is said that both pepsinogen I level and pepsinogen II/I ratio decrease in the patient with gastric cancer (Jpn. J. Cancer Res., 80, 111–114 (1989)).

Further, an attention is paid to serum pepsinogen II level and pepsinogen I/II ratio as markers of therapy for helicobacter pylori gastritis. That is to say, it is said that serum pepsinogen II level decreases significantly and pepsinogen I/II ratio increases significantly in a successful group consisting of patients in whom therapy resulted in eradication of the bacteria to compare with an unsuccessful group consisting of patients who remained infected (Prog. Med., 15, 1862–1868 (1995)).

Therefor, assaying the level of human pepsinogen II in human blood or urine may be useful for diagnosis at early stage of diseases such as gastric cancer, gastric ulcer and duodenal ulcer etc.

As for a method for assaying human pepsin which was obtained by activation of human pepsinogen, a method using human serum protein etc. in urine and serum based on its digesting activity has been known (Clin. Chem., 15, 1, 42–55 (1969)). The significance of clinical trial using such a method has been discussed, but it requires a long time. In addition, its accuracy was not good, so such a method has been of no practical use. Further, the results means the activity to digest protein, so it was reflected on the total activities of both pepsin I and pepsin II. Therefore it is impossible to determine the human serum pepsinogen II specifically.

Recently, a method for assaying human pepsinogen in urine (uropepsin) indirectly, based on inactivation of an acidic enzyme by activated pepsin was proposed (Japanese Patent Application Kokai Hei 7-155198). But the substrate used in this method did not show the specificity for pepsin II. It is said that the pepsinogen in urine is pepsinogen I. But, pepsin II may be also secreted in urine in some body condition, so it is difficult to determine the accurate level of pepsin II. It is impossible to assay the level of pepsinogen II in human serum specifically.

As for a method for assaying pepsinogen II, radio immunoassay (Kaku-igaku (in Japanese), Vol. 26, No. 9, 1217–1221 (1989)) and enzyme immunoassay (Japanese Patent Application Kokai Hei 7-304800) using a specific anti-body have been practical use, but these methods cause a radioactive pollution and require a long time and complicated procedure for assaying.

Some methods for assaying pepsin II using synthesized substrate have been proposed. For example, (A) in the paper of J. Med., Chem., 36, 2614 (1993), it was described that a peptide of the formula (A-1)

LysProAlaAlaPhePhe($NO_2$)ArgLeu (A-1) (SEQ ID NO:86)

(wherein Phe($NO_2$) is p-nitrophenylalanine.)

was used as a substrate in assaying inhibitory effect of some compounds on human pepsin II. That is to say, a peptide of the formula (A-1) was digested by human pepsin II to obtain a peptide of the formula (A-2)

Phe(NO2)ArgLeu (A-2)

(wherein Phe(NO2) is as defined hereinbefore.), and the obtained peptide of the formula (A-2) was used in the assaying inhibitory activity on enzyme based on decrease of absorbance at 234~324 nm as an index.

But this paper did not disclose that such a peptide of the formula (A-1) may be as a substrate for human pepsin II. Therefore, it is uncertain whether this peptide has specificity for human pepsin II, or not. In addition, the chromophore of this peptide is Phe($NO_2$), so it is expected that the accuracy of the method using this peptide is one tenth or less to compare with p-nitroaniline (abbreviated as pNA). Further, it is impossible to be used in automated clinical analyzer due to detection at 234~324 nm.

(B) in the paper of J. Biochem., 265, 871–878 (1990), it was described that a peptide of the formula (B-1)

LysProValValPhePhe($NO_2$)ArgLeu (B-1) (SEQ ID NO:87)

(wherein Phe($NO_2$) is as defined hereinbefore.), was used as a substrate in assaying inhibitory effect of some compounds on human pepsin II. That is to say, a peptide of the formula (B-1) was digested by human pepsin II to obtain a peptide of the formula (B-2)

Phe(NO2)ArgLeu (B-2)

(wherein Phe($NO_2$) is as defined hereinbefore.), and the obtained peptide of the formula (B-2) was used in the assaying inhibitory activity on enzyme based on decrease of absorbance at 234~324 nm as an index.

But this paper did not disclose that such a peptide of the formula (B-1) may be as a substrate for human pepsin II. Therefore, it is uncertain whether this peptide has a specificity for human pepsin II, or not. In addition, the chromophore of this peptide is Phe($NO_2$), so it is expected that the accuracy of the method using this peptide is one tenth or less to compare with p-nitroaniline (abbreviated as pNA). Further, it is impossible to be used in automated clinical analyzer due to detection at 234~324 nm (There are the same problems as in paper (A).).

(C) In CS-261172, it was described that a peptide of the formula (C-1)

X—A—B-Phe-D-pNA (C-1)

(wherein X is hydrogen, C3~5 carboxylalkylcarbonyl or C1~5 alkylcarbonyl,

A is pyroglutamic acid (abbreviated as pGlu), Asp, Glu or Gly residue or 2-oxoimidazoline-1-yl-carbonyl, B is His, Gly or Pro residue, D is Phe, Leu, Nle, Met or S—C1~3 alkyl-Cys residue, and pNA is p-nitroaniline residue.)

was used as a substrate in assaying activities of pepsin I, pepsin II and chymosin.

But, there was neither description nor suggestion about the specificity of this peptide for human pepsin II.

In the example, a peptide of the formula (C-2)

pGluHisPhePhe-pNA (C-2) (SEQ ID NO:88)

(wherein pGlu and pNA are as defined hereinbefore.)

was used in assaying activity of pig pepsin. This pig pepsin was not purified and thought to be a mixture of pepsin I and pepsin II. So, it is not expected that this substrate possesses a specificity for human pepsin II.

(D) In the paper of Clinica Chimica Acta 213, 103–110 (1992), it was described that a peptide of the formula (D-1)

$X^d$—($AA^d$)$n^d$-Phe-$D^d$-pNA (D-1)

(wherein $X^d$ is pGlu, Glt, $AA^d$ is sequence for a substrate for N-termini, $n^d$ is 1 or 2, $D^d$ is Phe, Nle or Met and the other symbols are as defined hereinbefore.)

was used as a substrate in assaying activities of pepsin I, pepsin II and chymosin.

But, there was neither description nor suggestion about the specificity of this peptide for human pepsin II.

In the experimental example, a peptide of the formula (D-2) or (D-3)

pGluHisPhePhe-pNA (D-2) or (SEQ ID NO:90)

pGluHisPheMet-pNA (D-3) (SEQ ID NO:91)

(wherein pGlu and pNA are as defined hereinbefore.)

was used as a substrate in assaying activities of pig pepsin. This pig pepsin was not purified and thought to be a mixture of pepsin I and pepsin II. So, it is not expected that this substrate possesses a specificity for human pepsin II.

(E) In the paper of Anal. Biochem., 234, 113 (1996), it was described that peptides of the formula (E-1) or (E-2)

AbzAlaAlaPhePheAlaAla-Ded (E-1), or (SEQ ID NO:92)

AbzAlaAlaPhePheAlaAla-pNA (E-2) (SEQ ID NO:93)

(wherein Abz is o-aminobenzoyl, Ded is N-2,4-dinitrophenylethylene-diamine and pNA is as defined hereinbefore.), were used as substrate in assaying activities of human pepsin I, human pepsin II, human cathepsin D and HIV protease by fluorophotometry.

In this paper, the fluorescent changes caused by modification of peptide was discussed. Particularly, a peptide of the formula (E-1) seemed to be suggested to have specificity for human pepsin I from the experimental result. But, the peptides of the formula (E-1) or (E-2) were not expected to have the specificity for human pepsin II.

(F) In the paper of J. Biol. Chem., 244, 5, 1085–1091 (1969), it was described that peptides of the formula (F-1) ~(F-5)

Z-TyrAla (F-1),

Z-TyrThr (F-2),

Z-TyrLeu (F-3),

Z-TyrSer (F-4) or

Z-TrpAla (F-5)

(wherein Z is benzyloxycarbonyl.)

were used as substrate in assaying activities of human pepsin II specifically. But it requires a long time and complicated procedure. In addition, its accuracy was not good, so such a method has been of no practical use.

The substrates described in the said five references (A)~(F) are distinct from the substrate (peptide) of the present invention entirely. That is to say, there is a structural characteristic that an amino acid of the formula

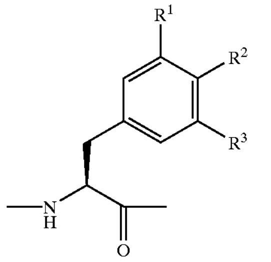

(wherein all the symbols are as defined hrereinbefore.) in the peptide of the formula (I) of the present invention is not an essential amino acid (for example, Phe, Tyr) but phenylalanine substituted by halogen or 2-naphthylalanine (in which naphthyl may be substituted by halogen.). Such a group was neither described nor suggested in the said six references (A)~(F).

DISCLOSURE OF THE INVENTION

The present inventors have been studying to dissolve these problems of the related arts and to find a substrate which is high-sensitive (being high rate of enzyme reaction i.e., digesting a substrate by human pepsin II at a high rate and/or being able to produce efficient coloring) and specific for human pepsin II, and then have succeeded in synthesizing a substrate (peptide) which is sensitive and specific for human pepsin II. By using this substrate, it become to possible to determine pepsin II for short time to compare with the method of related arts and to determine pepsinogen II and pepsin II using automated clinical analyzer.

That is to say, the present invention relates to 1) a peptide of the formula (I)

(I)

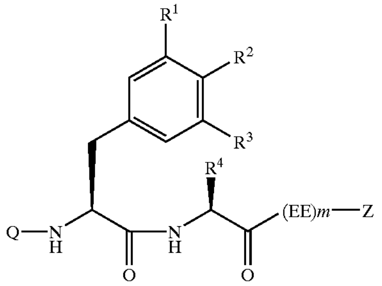

(wherein all the symbols are as defined hereinbefore.), or acid addition salt thereof, 2) a method for assaying human pepsinogen II or human pepsin II characterized by digesting a peptide of the formula (I) described in the above 1) (wherein all the symbols are as defined hereinbefore.), or an acid addition salt thereof, by human pepsin II which is obtained by activation of human pepsinogen II in a sample or human pepsin II in a sample to obtain an amino acid derivative of the formula (II)

(II)

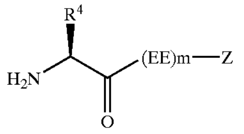

(wherein all the symbols are as defined hereinbefore.), digesting the obtained amino acid derivative by aminopeptidase to obtain an aniline, aminocoumarine or aminonaphthalene derivative of the formula Z—H and then detecting the obtained aniline, aminocoumarine or aminonaphthalene derivative, 3) a kit for assaying human pepsinogen II or human pepsin II which is characterized by comprising a peptide of the formula (I) described in the above 1), or an acid addition salt thereof as a substrate and aminopeptidase.

DETAILED EXPLANATION OF THE INVENTION

Figure 1:
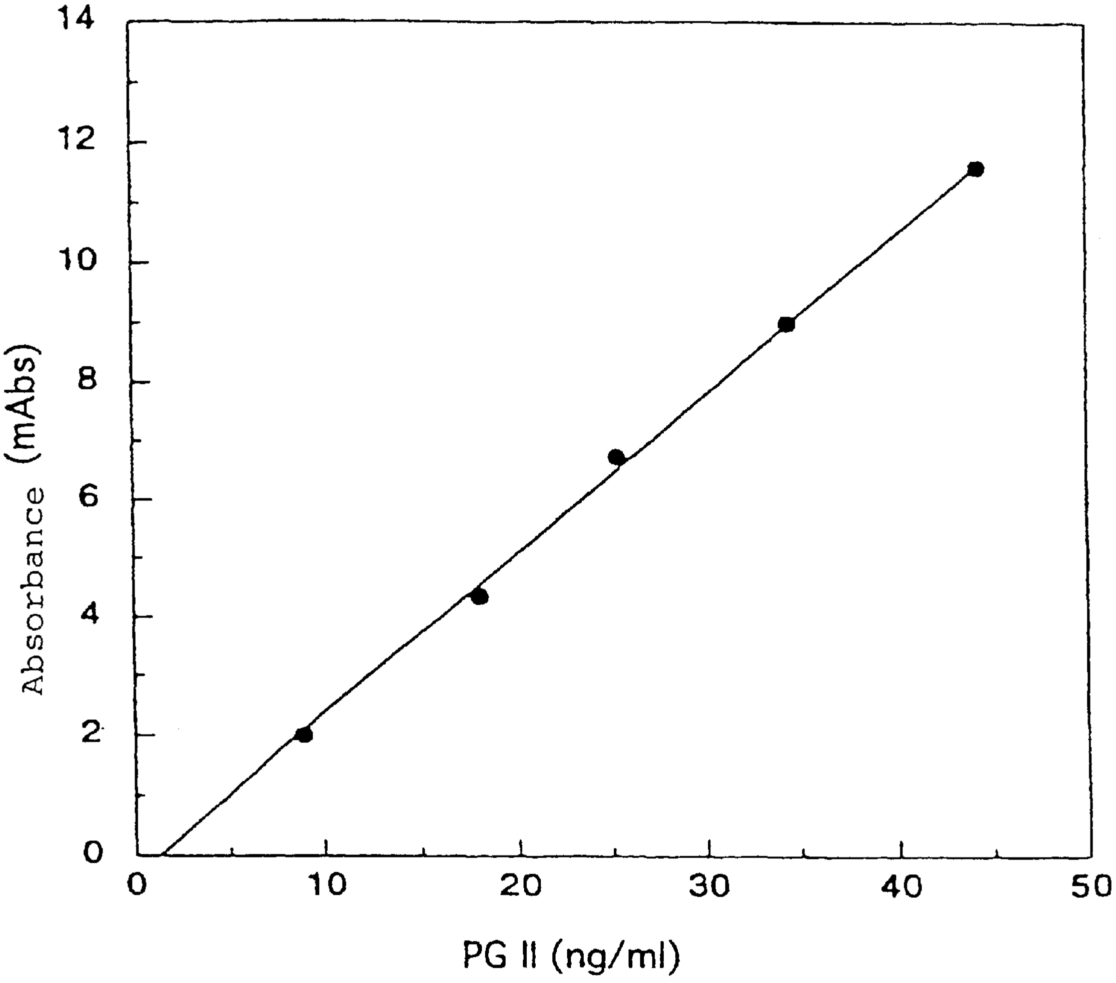
FIG. 1 shows calibration curve between pepsinogen II level (ng/ml) and the plotted increase of absorbance in Example 4.

A sample as an objet in the present invention means any sample to be determined the concentration of human pepsinogen II and activity of human pepsin II. For example, such a sample includes human body fluid (such as gastric juice, blood or urine etc.). The above pepsinogen II (pepsin II) exists as form of pepsinogen II in the body fluid such as blood or urine except for gastric juice, on the other hand, it exists as form of pepsin II in gastric juice.

The abbreviation consisting of three characters in the present invention means an amino acid (unless specified, it means L-type of α-amino acid.) well known and its definition is as follows:

Gly=glycine,

Ala=alanine.

Val=valine

Leu=leucine,

An amino-protective group represented by $Q^a$ in Q includes, for example, C1~6 alkylcarbonyl, C1~6 alkylsulfonyl, benzyloxycarbonyl, tert-butoxycarbonyl, 9-fluorenylmethoxycarbonyl or benzoyl or its derivative (in which benzene ring in benzyloxycarbonyl or benzoyl is unsubstituted or substituted by 1~5 of substituent(s) selected from the group consisting of nitro, amino, amino gourd substituted by one or two C1~6 alkyl, C1~6 hydroxyalkylamino, carboxyl, hydroxy, halogen, C1~6 alkyl, C1~6 alkoxy, thiol, sulfonyl, C1~6 alkylsulfonyl, —$CH_2CH_2COOH$ and —CH=CH—COOH).

A group of $NH_2$—($CH_2$)r—CO— represented by $Q^a$ in Q includes β-aminopropionic acid residue (β-Ala-), γ-aminobutanoic acid residue (γ-Abu-), δ-aminopentanoic acid residue, δ-aminocapronic acid residue, 6-aminoheptanoic acid residue, 7-aminooctanoic acid residue.

Amino acid residue represented by AA and EE in Q includes twenty essential amino acid (Gly, Ala, Val, Leu, lie, Ser, Thr, Asp, Glu, Asn, Gin, Lys, Arg, Cys, Met, Phe, Tyr, Trp, His, Pro) residue.

In these amino acids,

1) Gly, Ala, Val, Leu, lie, Ser, Thr, Asp, Glu, Asn, Gin, Lys, Arg, Cys, Met are aliphatic amino acids,
2) Phe, Tyr are aromatic amino acids,
3) Trp, His, Pro are heterocyclic amino acids.

In the aliphatic amino acid of 1), a) Val, Leu, Ile are branched amino acids, b) Ser, Thr are hydroxy amino acids, c) Asp, Glu are acidic amino acids, d) Asn, Gln are amides, e) Lys, Arg are basic amino acids, f) Cys, Met are S-containing amino acids.

Preferably, Q includes polypeptide of $Q^b$—(M)s—$A^1$— (in which $A^1$

IIe=isoleucine,

Ser=serine,

Thr=threonine,

Asp=aspartic acid,

Glu glutamic acid,

Asn=asparagin

Gln=gulutamine

Lys=lysine,

Arg=arginine,

Cys=cystein,

Met=methionine,

Phe=phenylalanine,

Tyr=tyrosine,

Trp=triptophane,

His=histidine,

Pro=proline.

As for the other abbreviation, its definition is as follows:

Sar=$N^{\alpha}$-methyl-glycine,

Me-Val=$N^{\alpha}$-methyl-valine,

Me-Ala=$N^{\alpha}$-methyl-alanine,

Nle=norleucine,

γ-Abu=γ-aminobutanoic acid,

Glt=glytaryl (—$CO(CH_2)_3CO$—), pNA=p-nitroaniline residue,

Ac=acetyl, 3,4-DCP=3,4-dichlorophenyl, m-ASD=m-anisidine residue,

DCHA=3,5-dichloro-4-hydroxyaniline residue.

C1~4 alkyl represented by $Q^a$ in Q and $Q^b$ described hereinafter includes methyl, ethyl, propyl or butyl, or isomer thereof.

is Gly, Ala, Ser, Asp, Glu, Asn, Gin or Met residue, s is an integer of 2, 3, 4 or 5, $Q^b$ is hydrogen, C1~4 alkyl, C1~6 alkylcalbonyl, D- or L-amino acid residue or $NH_2$—($CH_2$) r—CO— (in which r is as defined hereinbefore.), each AA is as defined hereinbefore.), more preferably, polypeptide of $Q^b$—(M)t—$A^2$—$A^{11}$— (in which $A^{11}$ is Gly, Ala, Glu, Asn residue, $A^2$ is Gly, Ala, Leu, Ser, Asp, Glu, Asn or Gin residue, t is an integer of 1, 2, 3 or 4, $Q^b$ and each AA are as defined hereinbefore.), most preferably, polypeptide of $Q^b$—(AA)t—$A^{22}$—$A^{11}$— (in which $A^{11}$ is Gly, Ala, Glu or Asn residue, $A^{22}$ is Gly, Ser, Glu or Gin residue, t, $Q^b$ and each AA are as defined hereinbefore.).

Aromatic carbon ring formed by $R^1$, $R^2$ and unsaturated bond together includes benzene or naphthalene ring, more preferably, benzene ring.

Each m is preferable.

An aniline, aminocoumarine or aminonaphthalene derivative represented by Z—H means unsubstituted aniline, unsubstituted aminocoumarin, and unsubstituted aminonaphthalene or substituted ones wherein benzene ring, coumarin ring, naphthalene ring in each group is substituted by 1~5 of substituent(s) selected from the group consisting of nitro, amino, amino gourd substituted by one or two C1~6 alkyl, C1~6 hydroxyalkylamino, carboxyl, hydroxy, halogen, C1~6 alkyl, C1~6 alkoxy, thiol, sulfonyl, C1~6 alkylsulfonyl, —$CH_2CH_2COOH$ and —CH=CH—COOH. Preferably, the number of such substituent(s) is 1, 2 or 3.

C1~6 alkyl in the explanation of the said aniline, aminocoumarine or aminonaphthalene derivative represented by Z—H and amino-protective group represented by $Q^a$ in Q, C1~6 alkyl in C1~6 alkylcarbonyl (including C1~6 alkyl represented by $Q^b$ described hereinafter) or C1~6 alkyl in C1~6 alkylsulphonyl and C1~6 hydroxyalkylamino includes methyl, ethyl, propyl, butyl, pentyl or hexyl, or isomer thereof.

C1~6 alkoxy in the explanation of the said aniline, aminocoumarine or aminonaphthalene derivative represented by Z—H and amino-protective group represented by $Q^a$ in Q, includes methoxy, ethoxy, propoxy, butoxy, pentyloxy or hexyloxy, or isomer thereof.

Aniline derivative represented by Z—H includes, for example, p-nitroaniline, m-anisidine, 3,5-dichloro-4-hydroxyaniline, 3,5-dibromo-4-hydroxyaniline, N',N'-diethylphenylenediamine or 3-carboxyl-4-hydroxyaniline.

Aminocoumarine derivative or aminonaphthalene derivative represented by Z—H includes, for example, 7-amino-4-methylcoumarin, 4-methyl-2-aminonaphthalene, or 4-methoxy-2-aminonaphthalene.

Preferably, group represented by Z—H includes, for example, p-nitroaniline, m-anisidine, 3,5-dichloro-4-hydroxyaniline, 7-amino-4-methylcoumarin, 4-methyl-2-aminonaphthalene, or 4-methoxy-2-aminonaphthalene. More preferably, it includes p-nitroaniline, m-anisidine or 3,5-dichloro-4-hydroxyaniline.

The peptide of the present invention may be converted into the corresponding acid additional salts. Water-soluble salts are preferable. Suitable acid addition salts, for example, are salts of inorganic acids, e.g., such as hydrochloric acid, hydrobromic acid, phosphonate, sulphonate, nitric acid etc., or salts of organic acids, e.g., succinate, citrate, lactate, malate, benzenesulfonate, acetate, trifluoroacetate or trifluoromethansulfate etc. Trifluoroacetate or trifluoromethansulfate are preferable.

Process for Preparing Peptides of the Present Invention

A peptide used as a substrate in the present invention may be prepared by the well-known methods in chemical synthesis of peptide. For example, as shown in Reaction scheme 1 or examples described hereinafter, a peptide of the present invention may be prepared by reacting resin to be solid phase (e.g., oxymresin) with an amino acid of the formula (III)

(III)

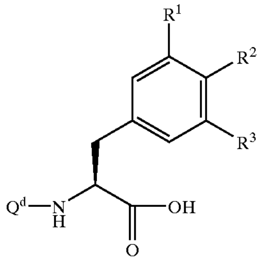

(in which $Q^d$ is an amino-protective group and the other symbols are as defined hereinbefore.), and then, by coupling reaction of the obtained compound with amino acid successively.

Further, as shown in Reaction scheme 2, a peptide of the present invention may be prepared by reacting an aniline, aminocoumarine or aminonaphthalene derivative of the formula Z—H as chromophore with an amino acid of the formulae (IV-1) or (IV-2)

(IV-2)

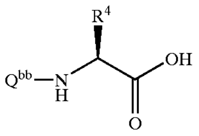

(wherein each $Q^{aa}$ and $Q^{bb}$ is an amino-protective group and the other symbols are as defined hereinbefore.), by coupling the obtained compound with an amino acid successively and by separating the aimed peptide from resin finally, if desired, followed by removal of protective group, or by coupling a few amino acids each other to obtain a few kind of polypeptides and then by coupling such a few kind of polypeptides successively.

Reaction scheme 1

Synthesis of peptide

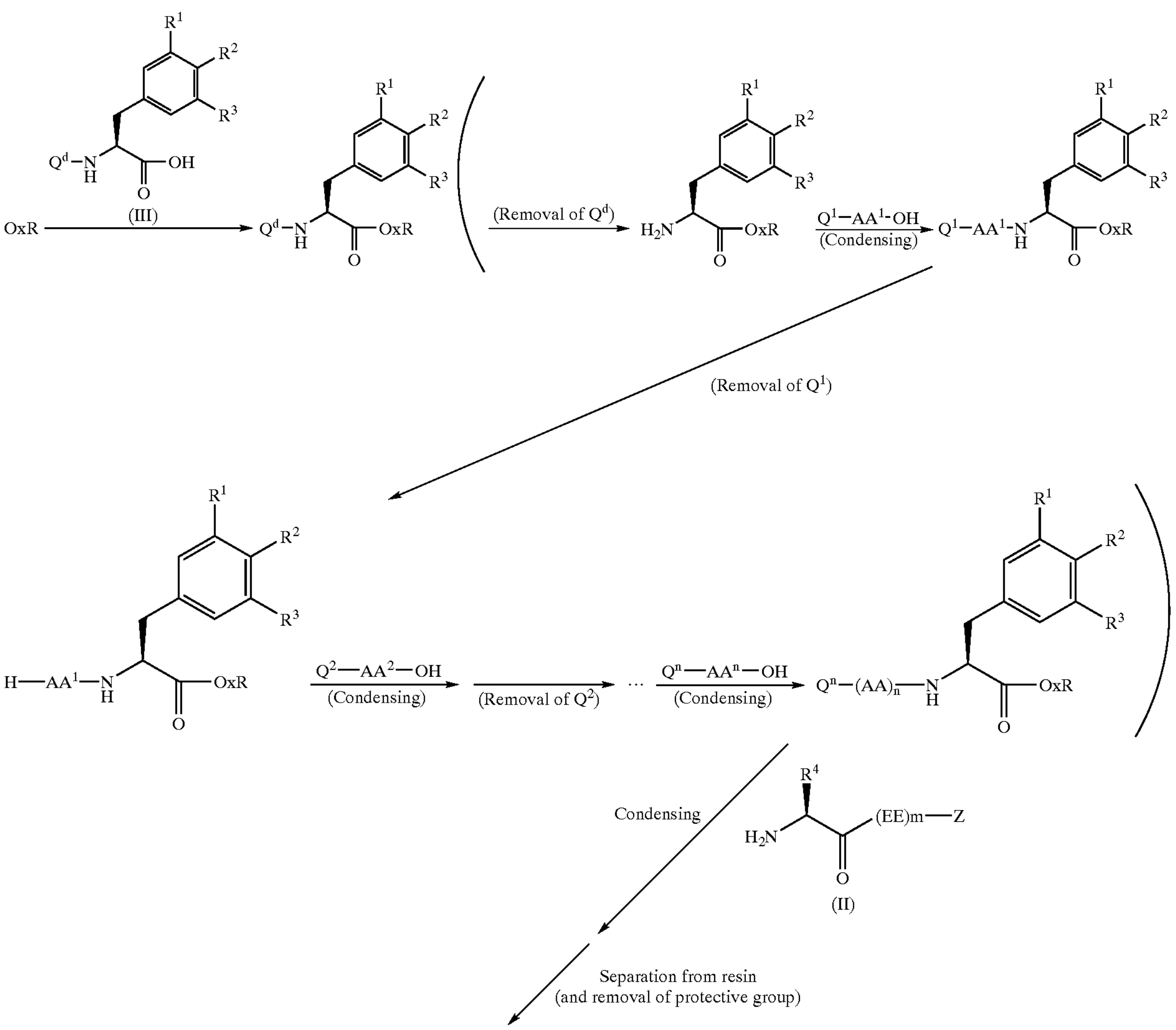

-continued
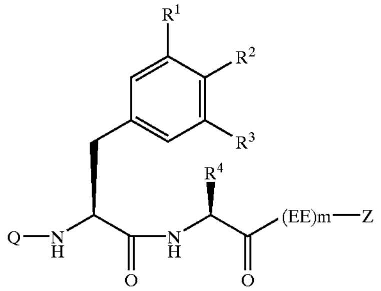
(I)
(in Reaction scheme 1, each $Q^d$, $Q^1$, $Q^2$ and $Q^n$ is an amino-protective group, OxR is oxymresin, each $AA^1$, $AA^2$ and $AA^n$ is an amino acid residue and the other symbols are as defined hereinbefore. In addition, each reaction in parentheses of (condensing), (Removal of $Q^1$) etc. is optional reaction.)
<u>Reaction scheme 2</u>
Synthesis of peptide
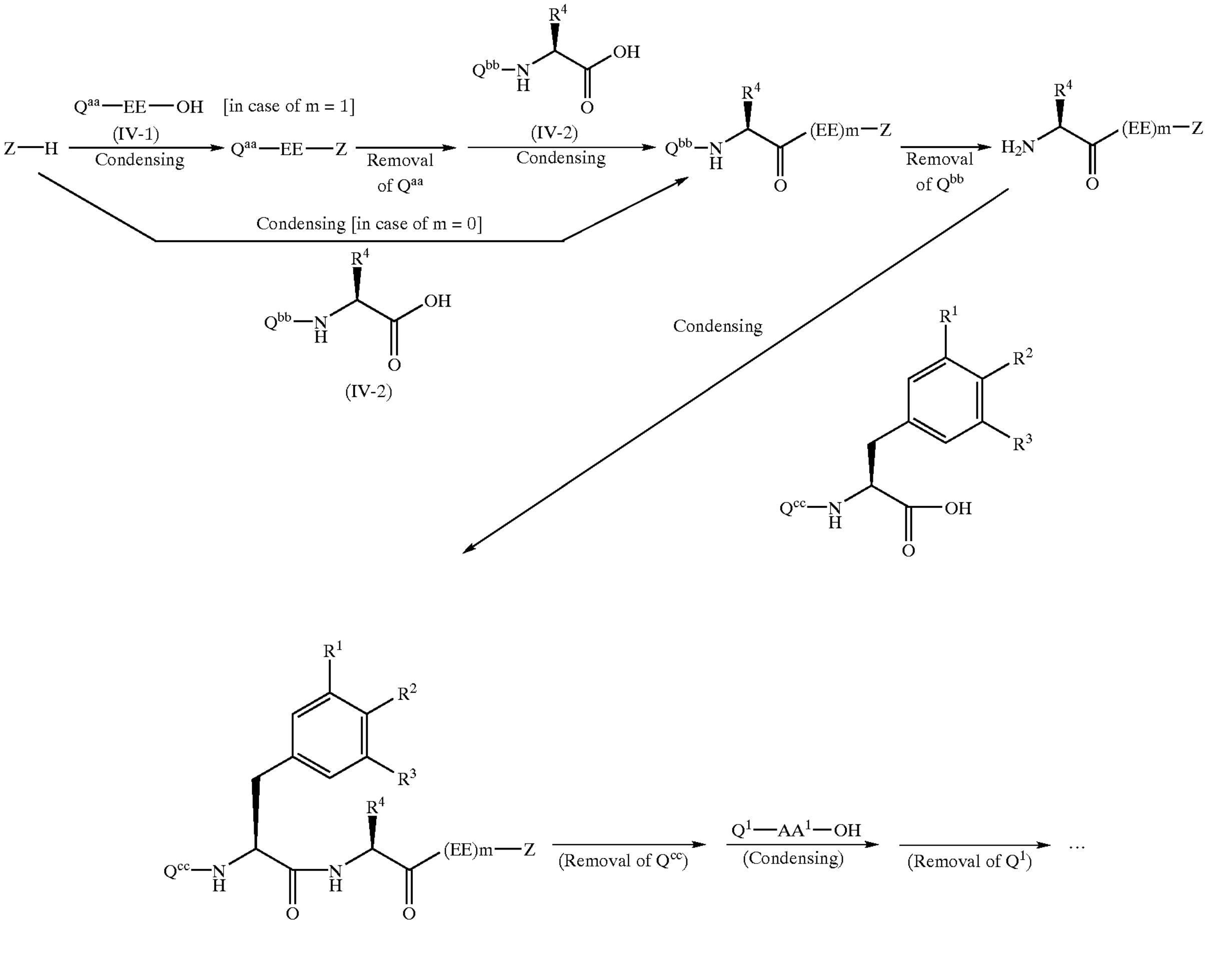

-continued

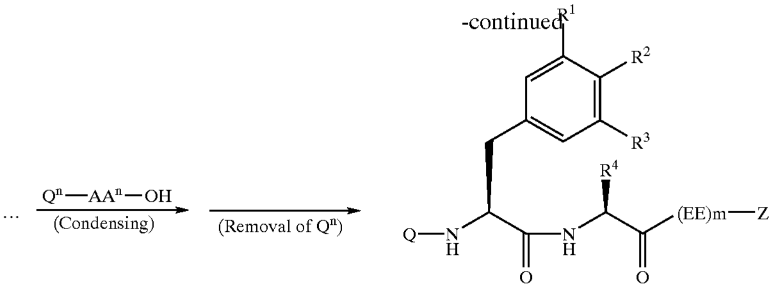

(I)

(in Reaction scheme 2, each $Q^{aa}$, $Q^{bb}$, $Q^{cc}$, $Q^1$, . . . $Q^n$ is an amino-protective group and the other symbols are as defined hereinbefore. In addition, each reaction in parentheses of (condensing), (Removal of $Q^1$) etc. is optional reaction.)

In the above coupling or reaction, amino and carboxyl group which does not relate to the reaction directly is protected by a protective group used ordinary in synthesizing a peptide. An amino-protective group represented by $Q^d$, $Q^1$, $Q^2$, $Q^n$, $Q^{aa}$, $Q^{bb}$ and $Q^{cc}$ includes, for example, benzyloxycarbonyl (CBZ), tert-butoxycarbonyl (Boc) or 9-fluorenylmethoxycarbonyl (Fmoc) etc. When an Arg or Lys is used in reaction, a δ-guanidino and ε-amino group in Arg and Lys, respectively, is protected by a protective group. A carboxyl-protective group represented by Rc includes, for example, ester group such as benzyl or tert-butyl ester etc. When Glu is used in reaction, the carboxyl group in the side chain is protected by a protective group. Each protective group is removable by the known method after reaction.

The coupling reaction of chromophore and amino acid may be carried out by the methods known per se, for example, (1) by the method using acid halide (2) by the method using mixed acid anhydride (3) by the method using conducing agent (EDC, PyBrop, DCC etc.)

Concrete description of the methods described above are as follows:

(1) method using acid halide may be carried out, for example, amino acid in which an amino group is protected (for example, amino acid of the formula $Q^1$—$AA^1$—OH, $Q^2$—$AA^2$—OH, $Q^n$—$AA^n$—OH etc.) is reacted with an acid halide (oxalyl chloride or thionyl chloride etc.) in an inert organic solvent (chloroform, methylene chloride, diethylether or THF (tetrahydrofuran) etc.) or without solvents at from −20° C. to a refluxing temperature to give an acid halide. The obtained acid halide and an aniline, aminocoumarine or aminonaphthalene derivative of the formula Z—H or a (poly)peptide prepared by coupling of the corresponding compound and then by removing an amino-protective group (for example, a (poly)peptide of the formula H—EE—Z or the formula

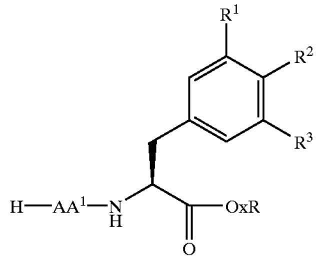

etc.) are reacted in an inert organic solvent (chloroform, methylene chloride, diethylether, THF etc.) in the presence of tertiary amine (pyridine, triethylamine, dimethylaniline, dimethylaminopyridine, diisopropylethylamine etc.) at 0~40° C.

(2) method using mixed acid anhydride may be carried out, for example, amino acid in which the amino group is protected (for example, amino acid of the formula $Q^1$—$AA^1$—OH, $Q^2$—$AA^2$—OH, $Q^n$—$AA^n$—OH etc.) is reacted with an acid halide (pivaloyl chloride, tosyl chloride, mesyl chloride etc.) or an acid derivative (ethyl chloroformate, isobutyl chloroformate etc.) in an inert organic solvent (chloroform, methylene chloride, diethyl ether, THF etc.) or without solvents, in the presence of tertiary amine (pyridine, triethylamine, dimethylaniline or dimethylaminopyridine etc.) at 0~40° C. to give mixed acid anhydride. The obtained mixed acid anhydride and an aniline, aminocoumarine or aminonaphthalene derivative of the formula Z—H or a (poly)peptide prepared by coupling of the corresponding compound and then by removing an amino-protective group (for example, a (poly)peptide of the formula H—EE—Z or the formula

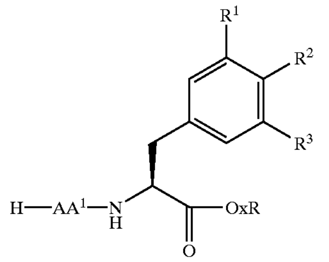

etc.) are reacted in an inert organic solvent (chloroform, methylene chloride, diethylether, THF etc.) at 0~70° C.

(3) method using condensing agent such as EDC (1-(3-dimethylaminopropyl)-3-ethylcarbodiimido), PyBrop (bromo-tris-pyrolydino-phosphoniumuhexafluorophosphate), DCC (dicyclohexylcarbodiimido) etc. may be carried out, for example; amino acid in which an amino group is protected (for example, amino acid of the formula $Q^1$—$AA^1$—OH, $Q^2$—$AA^2$—OH, $Q^n$—$AA^n$—OH etc.) and an aniline, aminocoumarine or aminonaphthalene derivative of the formula Z—H or a (poly)peptide prepared by coupling of the corresponding compound and then by removing an amino-protective group (for example, a (poly)peptide of the formula H—EE—Z or the formula

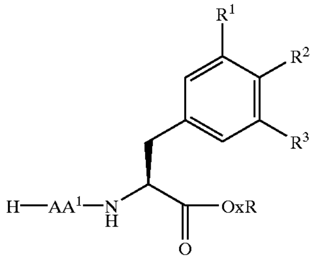

etc.) are reacted in an inert organic solvent (chloroform, methylene chloride, diethylether or THF etc.) or without solvents in the presence or absence of tertiary amine (pyridine, triethylamine, dimethylaniline, dimethylaminopyridine, diisopropylethylamine etc.) using EDC, PyBrop or DCC etc. at 0~40° C.

Preferably, these reactions (1), (2) and (3) described above are carried out under an atmosphere of inert gas (argon, nitrogen, etc.) on anhydrous condition.

Removal of a protective group may be carried out by the known method. For example, removal of CBZ or Bzl may be carried out under the atmosphere of hydrogen gas, in an organic solvent (methanol, ethanol or THF etc.) by using catalyst (Pd—C, Pd or Ni etc.) at 0~50° C. Removal of Boc may be carried out in a water-miscible organic solvent (methanol, ethanol, THF or dioxane etc.) by using organic acid (acetic acid, p-toluene sulfonic acid, trifluoro acetic acid or trichloro acetic acid etc.) or inorganic acid (hydrochloric acid or hydrobromic acid etc.) at 0~90° C. Removal of both Boc and Bzl at the same time may be carried out in the presence of thioanisole, m-chlezole etc. in trifloromethane sulfonic acid+trifluoro acetic acid or hydrogen fluoride.

In each reaction in the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

A peptide of the formula (I) may be converted into a corresponding acid addition salt thereof by the known method.

Starting Materials and Reagents

The starting materials and reagents in the present invention are known or may be prepared by known methods.

The Method for Assay

The enzymatic reaction used in the method for assaying of the present invention is shown in Reaction scheme 3.

Reaction scheme 3

Enzyme reaction (1) First reaction

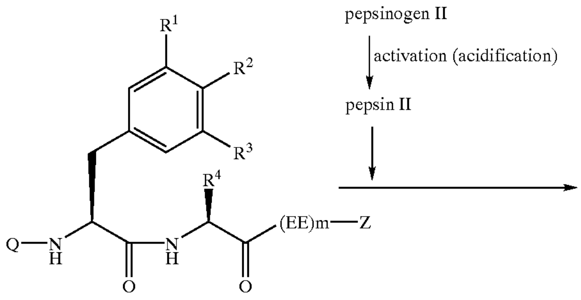

(I)

(II)

(2) Second reaction 1) in case of m = 0 in the formula (II)

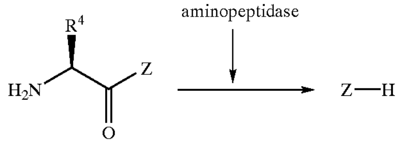

(II-1)

or 2) in case of m = 1 in the formula (II)

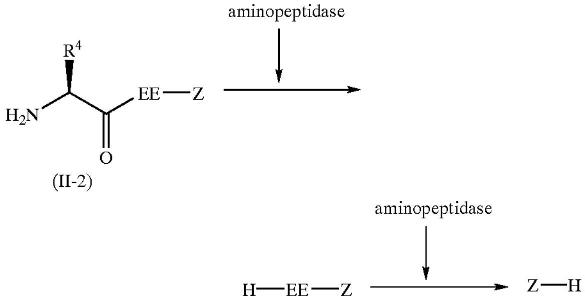

(II-2)

(in Reaction scheme 3, all the symbols are as defined hereinbefore.)

As for a sample, in case of body fluid except for gastric juice such as blood, urine etc., human pepsinogen II is activated to human pepsin II in the First reaction, and the obtained human pepsin II recognizes and digests a peptide of the formula (I) (wherein all the symbols are as defined hereinbefore.) or an acid addition salt thereof as a substrate, specifically. This activation of human pepsinogen II may be carried out, for example, under an acidic condition in combination with digesting a substrate at the same time or separately. As for this acidic condition, pH1.0~6.0 is preferable. A buffer includes tartaric acid, glycine, citric acid, oxalic acid, formic acid or and acetic acid buffer preferably. An amino acid derivative of the formula (II)

(II)

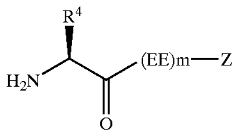

(wherein all the symbols are as defined hereinbefore.) which is released after digesting reaction is digested by aminopeptidase (for example, aminopeptidase M derived from pig kidney) at pH6~9 in Second reaction to release an aniline, aminocoumarine or aminonaphthalene derivative of the formula Z—H. It is possible to assay human pepsinogen II in a sample by detecting the obtained aniline, aminocoumarine or aminonaphthalene derivative.

On the other hand, in case of gastric juice, human pepsin II recognizes and digests a peptide of the formula (I) (wherein all the symbols are as defined hereinbefore.) or an acid addition salt thereof as a substrate under an acidic condition in First reaction specifically. As for this acidic condition, pH1.5~6.0 is preferable. A buffer includes tartaric acid, glycine, citric acid, oxalic acid, formic acid, or acetic acid buffer preferably. An amino acid derivative of the formula (II) which is released after digesting reaction is digested similarly to give an aniline, aminocoumarine or aminonaphthalene derivative. It is possible to assay human pepsin II in a sample by detecting the obtained aniline, aminocoumarine or aminonaphthalene derivative.

The detecting an aniline derivative may be carried out by the assaying the increase in absorbance of aniline derivative itself or by the assaying corresponding adequate coloring agent. An aniline derivative may be converted into a corresponding adequate coloring agent by reacting the said aniline derivative under an acidic condition to give diazo chromophore. The concrete material for diazo-coupling includes, 3,5-xylenol, N-ethyl-N-(2-hydroxy-3-sulfopropyl)-3,5-dimethylaniline or its salt (MAOS) etc. Such a converting may be carried out by addition of metal kilate complex such as pentacyanoamine feroate etc., by oxidizing and condensing a phenol derivative, aniline derivative such as N-ethyl-N-(3-sulfopropyl)-3-methoxyaniline (ADPS) etc. or xylenol derivative etc. and $NalO_4$ or by oxidizing and condensing with using oxidase such as bilirubin oxidase, polyphenol oxidase or ascorbic acid oxidase.

The detecting an aminocoumarine derivative, aminonaphthalene derivative is carried out by fluorometery (for example, λex=380 nm, λem=460 nm on 7-amino-4-methylcoumarin; λex=335 nm, λem=410 nm on 4-methyl-2-aminonaphthalene).

INDUSTRIAL AVAILABILITY

A peptide of the formula (i) or an acid addition salt thereof of the present invention is a substrate possessing the specificity for human pepsin II and high sensitivity (digesting a substrate by pepsin II at a high rate and/or being able to produce efficient coloring). Therefore, a method for assaying human pepsin II or human pepsinogen II by using a peptide or an acid addition salt thereof of the present invention is useful for diagnosis of gastric diseases such as gastric cancer, gastric ulcer etc. and contributes to the clinical field.

BEST MODE TO CARRY OUT THE INVENTION

The following examples are intended to illustrate, but not limit, the present invention. The solvents in parentheses of NMR show solvents used in determination. The meaning of abbreviation is as follows:

2-Naph=2-naphthyl, p-NA=p-nitroaniline,

Boc=tert-butoxycarbonyl,

OxR=oxymresin,

Bop=Bop reagent: benzotriazole-1-yloxytris (dimethylamino)-phosphoniumhexafluorophosphate, DMF=N, N-dimethylformamide, DIPEA=diisopropylethylamine, Bzl=benzyl, TFA=trifluoroacetic acid, TFMSA=trifluoromethansulphonic acid.

EXAMPLE 1

Synthesis of the Peptide of the Formula ProLeuSerGluAla(2-Naph)Ala-pNA (SEQ ID NO:f1)

1(1): Forming Solid Phase to Connect Resin (BocAla(2-Naph)-OxR)

Oxymresin (100 mg) was put into polystyrene column and swelled by addition of dichloromethan (1.0 ml) thereto. To a solution of butanol (1 M) and Bop in DMF (1 M) (150 μl), a solution of BocAla(2-Naph)—OH in DMF (1 M) (150 μl) was added. DIPEA (43 μl) was added thereto at 0° C. The mixture was stirred and added to the said polystyrene column. After stirring the mixture for 18 hours, the reaction mixture was stirred, filtered and washed with DMF three times and toluene three times successively to give BocAla (2-Naph)-OxR. The obtained compound was used in the next reaction without purification.

1(2): Lengthening Amino Acid Chain (BocProLeuSer(Bzl)Glu (Bzl)Ala(2-Naph)-OxR)

Into BocAla(2-Naph)-OxR (prepared in Example 1(1).) in polystyrene column, a solution of 20%TFA/toluene (3 ml) was added. After stirring the mixture for 2 hours, the reaction mixture was stirred, filtered and washed with toluene two times, isopropanol one time and DMF three times successively. To a solution of butanol (1 M) and Bop in DMF (1 M) (150 μl), a solution of BocGlu(Bzl)—OH in DMF (1 M) (150 μl) was added. DIPEA (43 μl) was added thereto at 0° C. The solution was stirred and added to the said polystyrene column. After stirring the mixture for 20 hours, the reaction mixture was stirred, filtered and washed with DMF three times and toluene three times successively to obtain BocGlu(Bzl)Ala(2-Naph)-OxR.

By the same procedure as above, the obtained compound was reacted to condense with Ser(Bzl), Leu and Pro successively to give BocProLeuSer(Bzl)Glu(Bzl)Ala(2-Naph)-OxR. The obtained compound was used in the next reaction without purification 1(3): Separation of Amino Acid from Resin To BocProLeuSer(Bzl)Glu(Bzl)Ala(2-Naph)-OxR (prepared in Example 1(2).), a solution of AlapNA·HCl (0.25 M), DIPEA (0.25 M) and acetic acid in DMF (0.25 M) (1000 μl) was added. The mixture was stirred for 24 hours and extracted with DMF three times. The extract was distilled off under reduced pressure, distilled water (10 ml) was added thereto. The mixture was stirred and filtered. The residue was washed with distilled water. The residue was dissolved into acetonitlile (20 ml). Toluene (10 ml) was added thereto. The mixture was dried under reduced pressure. The obtained crude was dissolved into TFA (4 ml). m-Cresol (200 μl) and TFMSA (80 ml) were added thereto at 0° C. The mixture was stirred for 2 hours. TFA was distilled off under reduced pressure. The residue was added dropwise to diethyl ether (300 ml) with stirring at 0° C. The precipitate was separated with centrifugation. The obtained precipitate was washed with iced ether (10 ml) three times, dried under reduced pressure. The obtained crude was dissolved into 30% acetonitolile and purified with C18-HPLC-column to give the title compound (20.3 mg) having the following physical data.

MS: (M+H)m/z=833; NMR: ($CD_3OD$) δ=8.18 (2H, d), 7.81 (2H, d), 7.78–7.70 (4H, M), 7.41–7.37 (3H, M), 4.77 (1H, dd), 4.50–4.26 (5H, M), 3.86 (1H, dd), 3.75 (1H, dd), 3.39 (2H, dd), 3.12 (2H, dd), 2.48–2.37 (1H, M), 2.25 (2H, t), 2.16–2.08 (1H, M), 2.07–1.94 (4H, M), 1.88–1.60 (5H, M), 1.45 (3H, d), 0.97–0.92 (6H, M).

EXAMPLES 2(1)~2(83)

By the same procedure as Example 1 with using various kinds of amino acid and amino acid derivatives of the formula (II-A)

(II-A)

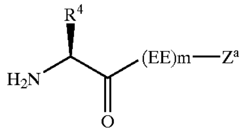

(in which $Z^a$ is an aniline derivative residue and the other symbols are as defined hereinbefore.), the peptides of the formula (I-B) having the following physical data were obtained. The results are shown in Table 2 (Tables 2-1~2-6).

(I-B)

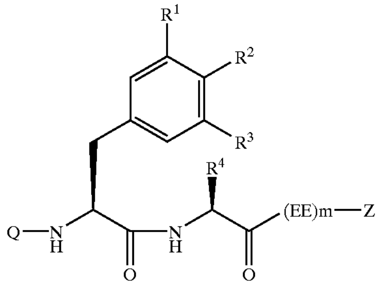

TABLE 2

| Example No. | Q | Definition of each symbol 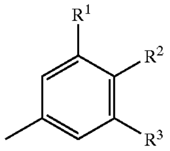 | $R^4$ | (EE)m | Z | Salt | SEQ ID NO: | MALDI positive m/z (M + H)+ | (M + Na)+ | (M + K)+ |
|---|---|---|---|---|---|---|---|---|---|---|
| 2(1) | Leu Ser | 4-I-Phenyl | H | single bond | p-NA | TFA | SEQ ID NO:2 | 669 | 691 | |
| 2(2) | Pro Gln Gln Ala | 2-Naphthyl | H | single bond | p-NA | TFA | SEQ ID NO:3 | 817 | 839 | 855 |
| 2(3) | Pro Gln Gln Ala | 4-I-Phenyl | H | single bond | p-NA | TFA | SEQ ID NO:4 | 893 | 915 | 931 |
| 2(4) | Pro Gln Gln Ala | 4-Cl-Phenyl | H | single bond | p-NA | TFA | SEQ ID NO:5 | 801 | 823 | 839 |
| 2(5) | Pro Gln Gln Ala | 2-Naphthyl | Me | single bond | p-NA | TFA | SEQ ID NO:6 | 831 | 853 | 869 |
| 2(6) | Pro Gln Gln Ala | 4-I-Phenyl | Me | single bond | p-NA | TFA | SEQ ID NO:7 | 907 | 929 | 945 |
| 2(7) | Pro Gln Gln Ala | 4-Cl-Phenyl | Me | single bond | p-NA | TFA | SEQ ID NO:8 | 815 | 837 | 853 |
| 2(8) | Pro Gln Gln Ala | 2-Naphthyl | Et | single bond | p-NA | TFA | SEQ ID NO:9 | 845 | 867 | 883 |
| 2(9) | Pro Gln Gln Ala | 4-I-Phenyl | Et | single bond | p-NA | TFA | SEQ ID NO:10 | 921 | 943 | |
| 2(10) | Pro Gln Gln Ala | 4-Cl-Phenyl | Et | single bond | p-NA | TFA | SEQ ID NO:11 | 829 | 851 | |
| 2(11) | Pro Gln Gln Ala | 2-Naphthyl | n-Pr | single bond | p-NA | TFA | SEQ ID NO:12 | 859 | 881 | 897 |
| 2(12) | Pro Gln Gln Ala | 4-I-Phenyl | n-Pr | single bond | p-NA | TFA | SEQ ID NO:13 | 935 | 957 | 973 |
| 2(13) | Pro Gln Gln Ala | 4-Cl-Phenyl | n-Pr | single bond | p-NA | TFA | SEQ ID NO:14 | 843 | 865 | 881 |
| 2(14) | Ac Lys Pro Gln Gln Ala | 4-I-Phenyl | Me | single bond | p-NA | TFA | SEQ ID NO:15 | 1077 | 1099 | 1115 |
| 2(15) | Leu Pro Gln Gln Ala | 4-I-Phenyl | Me | single bond | p-NA | TFA | SEQ ID NO:16 | 1020 | 1042 | 1058 |
| 2(16) | Asn Pro Gln Gln Ala | 4-I-Phenyl | Me | single bond | p-NA | TFA | SEQ ID NO:17 | 1021 | 1043 | |
| 2(17) | Gln Pro Gln Gln Ala | 4-I-Phenyl | Me | single bond | p-NA | TFA | SEQ ID NO:18 | 1035 | 1057 | 1073 |
| 2(18) | Ala Pro Gln Gln Ala | 4-I-Phenyl | Me | single bond | p-NA | TFA | SEQ ID NO:19 | 978 | 1000 | 1016 |
| 2(19) | Val Pro Gln Gln Ala | 4-I-Phenyl | Me | single bond | p-NA | TFA | SEQ ID NO:20 | 1006 | 1028 | 1044 |
| 2(20) | Gly Pro Gln Gln Ala | 4-I-Phenyl | Me | single bond | p-NA | TFA | SEQ ID NO:21 | 964 | 986 | 1002 |
| 2(21) | Phe Pro Gln Gln Ala | 4-I-Phenyl | Me | single bond | p-NA | TFA | SEQ ID NO:22 | 1054 | 1076 | 1092 |
| 2(22) | Pro Gln Gln Asn | 2-Naphthyl | Me | single bond | p-NA | TFA | SEQ ID NO:23 | 874 | | |
| 2(23) | Pro Gln Gln Gln | 2-Naphthyl | Me | single bond | p-NA | TFA | SEQ ID NO:24 | 888 | 910 | 926 |
| 2(24) | Pro Gln Gln Gly | 2-Naphthyl | Me | single bond | p-NA | TFA | SEQ ID NO:25 | 817 | 839 | 855 |
| 2(25) | Pro Gln Gln Met | 2-Naphthyl | Me | single bond | p-NA | TFA | SEQ ID NO:26 | 891 | | |
| 2(26) | Pro Gln Gln Ser | 2-Naphthyl | Me | single bond | p-NA | TFA | SEQ ID NO:27 | 847 | 869 | |
| 2(27) | Pro Gln Gln Asp | 2-Naphthyl | Me | single bond | p-NA | TFA | SEQ ID NO:28 | 875 | 897 | 913 |
| 2(28) | Pro Gln Gln Glu | 2-Naphthyl | Me | single bond | p-NA | TFA | SEQ ID NO:29 | 889 | 911 | |
| 2(29) | Pro Gln Asn Glu | 2-Naphthyl | Me | single bond | p-NA | TFA | SEQ ID NO:30 | 875 | 897 | |
| 2(30) | Pro Gln Ala Glu | 2-Naphthyl | Me | single bond | p-NA | TFA | SEQ ID NO:31 | 832 | | |
| 2(31) | Pro Gln Gly Glu | 2-Naphthyl | Me | single bond | p-NA | TFA | SEQ ID NO:32 | 818 | | |
| 2(32) | Pro Gln Leu Glu | 2-Naphthyl | Me | single bond | p-NA | TFA | SEQ ID NO:33 | 874 | 896 | |
| 2(33) | Pro Gln Glu Glu | 2-Naphthyl | Me | single bond | p-NA | TFMSA | SEQ ID NO:34 | 890 | 912 | 928 |
| 2(34) | Pro Gln Asp Glu | 2-Naphthyl | Me | single bond | p-NA | TFMSA | SEQ ID NO:35 | 876 | 898 | |
| 2(35) | Pro Gln Ser Glu | 2-Naphthyl | Me | single bond | p-NA | TFMSA | SEQ ID NO:36 | 848 | 870 | 886 |

TABLE 2-continued

| Example No. | Q | 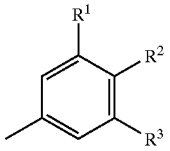 | $R^4$ | (EE)m | Z | Salt | SEQ ID NO: | MALDI positive m/z (M + H)+ | (M + Na)+ | (M + K)+ |
|---|---|---|---|---|---|---|---|---|---|---|
| | Definition of each symbol | | | | | | | | | |
| 2(36) | Pro Asn Ser Glu | 2-Naphthyl | Me | single bond | p-NA | TFMSA | SEQ ID NO:37 | 834 | 856 | |
| 2(37) | Pro Ala Ser Glu | 2-Naphthyl | Me | single bond | p-NA | TFMSA | SEQ ID NO:38 | 791 | 813 | |
| 2(38) | Pro Val Ser Glu | 2-Naphthyl | Me | single bond | p-NA | TFMSA | SEQ ID NO:39 | 819 | 841 | |
| 2(39) | Pro Met Ser Glu | 2-Naphthyl | Me | single bond | p-NA | TFMSA | SEQ ID NO:40 | 851 | 873 | 889 |
| 2(40) | Pro Ile Ser Glu | 2-Naphthyl | Me | single bond | p-NA | TFMSA | SEQ ID NO:41 | 833 | 855 | |
| 2(41) | Pro Gly Ser Glu | 2-Naphthyl | Me | single bond | p-NA | TFMSA | SEQ ID NO:42 | 777 | 799 | |
| 2(42) | Pro Glu Ser Glu | 2-Naphthyl | Me | single bond | p-NA | TFMSA | SEQ ID NO:43 | 849 | 871 | 887 |
| 2(43) | Pro Asp Ser Glu | 2-Naphthyl | Me | single bond | p-NA | TFMSA | SEQ ID NO:44 | 835 | | |
| 2(44) | Pro Ser Ser Glu | 2-Naphthyl | Me | single bond | p-NA | TFMSA | SEQ ID NO:45 | 807 | 829 | 845 |
| 2(45) | Pro Thr Ser Glu | 2-Naphthyl | Me | single bond | p-NA | TFMSA | SEQ ID NO:46 | 821 | 843 | 859 |
| 2(46) | Asn Leu Ser Glu | 2-Naphthyl | Me | single bond | p-NA | TFMSA | SEQ ID NO:47 | 850 | 872 | 888 |
| 2(47) | Ala Leu Ser Glu | 2-Naphthyl | Me | single bond | p-NA | TFMSA | SEQ ID NO:48 | 807 | 829 | 845 |
| 2(48) | Val Leu Ser Glu | 2-Naphthyl | Me | single bond | p-NA | TFMSA | SEQ ID NO:49 | 835 | 857 | 873 |
| 2(49) | Met Leu Ser Glu | 2-Naphthyl | Me | single bond | p-NA | TFMSA | SEQ ID NO:50 | 867 | 889 | 905 |
| 2(50) | Ile Leu Ser Glu | 2-Naphthyl | Me | single bond | p-NA | TFMSA | SEQ ID NO:51 | 849 | 871 | 887 |
| 2(51) | Gly Leu Ser Glu | 2-Naphthyl | Me | single bond | p-NA | TFMSA | SEQ ID NO:52 | 793 | 815 | 831 |
| 2(52) | Leu Leu Ser Glu | 2-Naphthyl | Me | single bond | p-NA | TFMSA | SEQ ID NO:53 | 849 | 871 | 887 |
| 2(53) | Gln Leu Ser Glu | 2-Naphthyl | Me | single bond | p-NA | TFMSA | SEQ ID NO:54 | 864 | | |
| 2(54) | Lys Leu Ser Glu | 2-Naphthyl | Me | single bond | p-NA | TFMSA | SEQ ID NO:55 | 864 | 886 | 902 |
| 2(55) | Glu Leu Ser Glu | 2-Naphthyl | Me | single bond | p-NA | TFMSA | SEQ ID NO:56 | 865 | 887 | 903 |
| 2(56) | Ser Leu Ser Glu | 2-Naphthyl | Me | single bond | p-NA | TFMSA | SEQ ID NO:57 | 823 | 845 | 861 |
| 2(57) | Thr Leu Ser Glu | 2-Naphthyl | Me | single bond | p-NA | TFMSA | SEQ ID NO:58 | 837 | 859 | 875 |
| 2(58) | Tyr Leu Ser Glu | 2-Naphthyl | Me | single bond | p-NA | TFMSA | SEQ ID NO:59 | 899 | 921 | 937 |
| 2(59) | Ac Lys Leu Ser Glu | 2-Naphthyl | Me | single bond | p-NA | TFMSA | SEQ ID NO:60 | 906 | 928 | 944 |
| 2(60) | Pro Asn Leu Ser Glu | 2-Naphthyl | Me | single bond | p-NA | TFMSA | SEQ ID NO:61 | 947 | 969 | |
| 2(61) | Ac Lys Asn Leu Ser Glu | 2-Naphthyl | Me | single bond | p-NA | TFMSA | SEQ ID NO:62 | 1020 | 1042 | 1058 |
| 2(62) | Pro Ser Asn Leu Ser Glu | 2-Naphthyl | Me | single bond | p-NA | TFMSA | SEQ ID NO:63 | 1034 | 1056 | |
| 2(63) | Pro Asn Asn Leu Ser Glu | 2-Naphthyl | Me | single bond | p-NA | TFMSA | SEQ ID NO:64 | 1061 | | |
| 2(64) | Pro Gly Asn Leu Ser Glu | 2-Naphthyl | Me | single bond | p-NA | TFMSA | SEQ ID NO:65 | 1004 | 1026 | 1042 |
| 2(65) | Ac Lys Ala Leu Ser Glu | 2-Naphthyl | Me | single bond | p-NA | TFMSA | SEQ ID NO:66 | 977 | 999 | |
| 2(66) | β-Ala Asn Leu Ser Glu | 2-Naphthyl | Me | single bond | p-NA | TFMSA | SEQ ID NO:67 | 921 | 943 | 959 |
| 2(67) | Sar Asn Leu Ser Glu | 2-Naphthyl | Me | single bond | p-NA | TFMSA | SEQ ID NO:68 | | 943 | |
| 2(68) | Me-Val Leu Ser Glu | 2-Naphthyl | Me | single bond | p-NA | TFMSA | SEQ ID NO:69 | 849 | 871 | 887 |
| 2(69) | Me-Ala Leu Ser Glu | 2-Naphthyl | Me | single bond | p-NA | TFMSA | SEQ ID NO:70 | 821 | 843 | |
| 2(70) | Sar Leu Ser Glu | 2-Naphthyl | Me | single bond | p-NA | TFMSA | SEQ ID NO:71 | 807 | 829 | |
| 2(71) | Pro Leu Ser Glu | 4-Cl-Phenyl | Me | single bond | p-NA | TFMSA | SEQ ID NO:72 | 817 | 839 | 855 |
| 2(72) | Pro Leu Ser Glu | 3,4-DCP | Me | single bond | p-NA | TFMSA | SEQ ID NO:73 | 851 | 873 | |
| 2(73) | Val Leu Ser Glu | 4-Cl-Phenyl | Me | single bond | p-NA | TFMSA | SEQ ID NO:74 | 819 | 841 | |
| 2(74) | D-Ala Asn Leu Ser Glu | 2-Naphthyl | Me | single bond | p-NA | TFMSA | SEQ ID NO:75 | 921 | 943 | |
| 2(75) | D-Ala Leu Ser Glu | 2-Naphthyl | Me | single bond | p-NA | TFMSA | SEQ ID NO:76 | 807 | 829 | 845 |
| 2(76) | β-Ala Leu Ser Glu | 2-Naphthyl | Me | single bond | p-NA | TFMSA | SEQ ID NO:77 | 807 | 829 | 845 |
| 2(77) | γ-Abu Leu Ser Glu | 2-Naphthyl | Me | single bond | p-NA | TFMSA | SEQ ID NO:78 | 821 | 843 | 859 |
| 2(78) | Leu Ser Glu | 2-Naphthyl | Me | Leu | p-NA | TFMSA | SEQ ID NO:79 | | 871 | 887 |
| 2(79) | Leu Ser Glu | 2-Naphthyl | Me | Ala | p-NA | TFMSA | SEQ ID NO:80 | 807 | 829 | 845 |
| 2(80) | Leu Ser Glu | 2-Naphthyl | Me | Gly | p-NA | TFMSA | SEQ ID NO:81 | 793 | 815 | 831 |
| 2(81) | Sar Leu Ser Glu | 2-Naphthyl | Me | Ala | p-NA | TFMSA | SEQ ID NO:82 | 878 | 900 | 916 |
| 2(82) | Sar Leu Ser Glu | 2-Naphthyl | Me | Gly | p-NA | TFMSA | SEQ ID NO:83 | 864 | 886 | 902 |
| 2(83) | Sar Leu Ser Glu | 2-Naphthyl | Me | Ala | m-ASD | TFMSA | SEQ ID NO:84 | 863 | 885 | 901 |
| 2(84) | Sar Ser Gly | 2-Naphthyl | Me | Ala | DCHA | TFMSA | SEQ ID NO:85 | 732 | 754 | 770 |

(In Table 2, various symbols are as defined hereinbefore.)

EXAMPLES 3

Assaying Pepsin I and II on Digesting the Substrate of the Present Invention

Reagent

Tartaric acid buffer or glycine buffer (pH2.0) containing each peptide (0.5 mM) prepared in Examples 1 and 2(3) etc. (Examples in Table 3 described hereinafter).

Enzyme Solution I

An aqueous solution of human pepsin I or human pepsin II (0.01 mg/ml)

Method for Assay (1) Assay by HPLC

Enzyme solution I (0.1 ml) was added to Reagent (1.0 ml). After incubation of the mixture at 37° C. for 10, 30, 60 minutes, the mixture solution (0.3 ml) was collected. To the collected solution, 2N-NaOH (0.025 ml) was added to terminate the reaction. After addition of 2N-HCl (0.025 ml) to the mixture, protein was removed by the ultrafiltration. The assaying the amino acid derivatives of the formula (II-A)

(II-A)

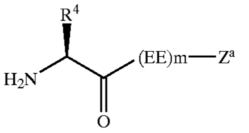

(in which all the symbols are as defined hereinbefore.)

which was released after digesting by human pepsin in the obtained solution was carried out by HPLC using C18 column. The ratio of digesting rate of pepsin II/pepsin I was calculated according to the result from assay by HPLC. Such assay is carried out to confirm that a substrate was digested by pepsin I or pepsin II correctly and that the amino acid derivatives of the formula (II-A) were released. The results are shown in Table 3 (Tables 3-1~3-3).

(In Table 3, all the symbols are as defined hereinbefore.)

As is shown clearly from the above Table, we understand that a peptide of the present invention has the specificity for pepsin II.

EXAMPLE 4

Assaying Human Pepsinogen II by the Method of the Present Invention (Calibration Curve)

Reagent Solution I

Nα-Me-GlyLeuSerGluAla(2-Naph)Ala-pNA.TFMSA (SEQ ID NO:71)(prepared in Example 2(70).) was dissolved into tartaric acid buffer (50 mM, pH2.0) to be at concentration of 0.5 mM.

Reagent Solution II

Aminopeptidase (marketed from Sigma Co.) was dissolved into Tris-HCl buffer (1.0 M, pH8.5) to be at concentration of 3.4 U/ml.

TABLE 3

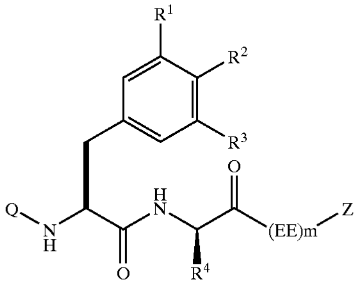

| | Definition of symbol | | | | | | | | | |
|---|---|---|---|---|---|---|---|---|---|---|
| Example No. | Q | 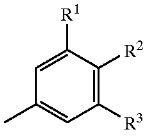 | $R^4$ | (EE)m | Z | salt | SEQ ID NO: | pepsin II digesting rate μM/min · 1 μg Enz | pepsin I digesting rate μM/min · 1 μg Enz | ration of digesting rate (pepsin II/ pepsin I) |
| 1 | Pro Leu Ser Glu | 2-Naphthyl | Me | single bond | p-NA | TFMSA | SEQ ID NO:1 | 55.40 | 0.2795 | 198.2 |
| 2(3) | Pro Gln Gln Ala | 4-I-Phenyl | H | single bond | p NA | TFA | SEQ ID NO:4 | 4.23 | 0.0020 | 2065.1 |
| 2(7) | Pro Gln Gln Ala | 4-Cl-Phenyl | Me | single bond | p-NA | TFA | SEQ ID NO:8 | 3.50 | 0.0335 | 104.4 |
| 2(11) | Pro Gln Gln Ala | 2-Naphthyl | n-Pr | single bond | p-NA | TFA | SEQ ID NO:12 | 4.10 | 0.0235 | 174.9 |
| 2(14) | Ac Lys Pro Gln Gln Ala | 4-I-Phenyl | Me | single bond | p-NA | TFA | SEQ ID NO:15 | 3.85 | 0.0094 | 410.2 |
| 2(16) | Asn Pro Gln Gln Ala | 4-I-Phenyl | Me | single bond | p-NA | TFA | SEQ ID NO:17 | 8.95 | 0.0082 | 1094.8 |
| 2(18) | Ala Pro Gln Gln Ala | 4-I-Phenyl | Me | single bond | p-NA | TFA | SEQ ID NO:19 | 9.20 | 0.0122 | 757.0 |
| 2(22) | Pro Gln Gln Asn | 2-Naphthyl | Me | single bond | p-NA | TEA | SEQ ID NO:23 | 12.87 | 0.0578 | 222.6 |
| 2(23) | Pro Gln Gln Gln | 2-Naphthyl | Me | single bond | p-NA | TFA | SEQ ID NO:24 | 5.90 | 0.0191 | 308.8 |
| 2(24) | Pro Gln Gln Gly | 2-Naphthyl | Me | single bond | p-NA | TFA | SEQ ID NO:25 | 12.06 | 0.0058 | 2081.6 |
| 2(25) | Pro Gln Gln Met | 2-Naphthyl | Me | single bond | p-NA | TFA | SEQ ID NO:26 | 5.56 | 0.0063 | 889.7 |
| 2(33) | Pro Gln Glu Glu | 2-Naphthyl | Me | single bond | p-NA | TFMSA | SEQ ID NO:34 | 25.41 | 0.0632 | 402.3 |
| 2(34) | Pro Gln Asp Glu | 2-Naphthyl | Me | single bond | p-NA | TFMSA | SEQ ID NO:35 | 15.40 | 0.0216 | 711.9 |
| 2(36) | Pro Asn Ser Glu | 2-Naphthyl | Me | single bond | p-NA | TFMSA | SEQ ID NO:37 | 21.22 | 0.1096 | 193.5 |
| 2(39) | Pro Met Ser Glu | 2-Naphthyl | Me | single bond | p-NA | TFMSA | SEQ ID NO:40 | 45.79 | 0.2277 | 201.1 |
| 2(45) | Pro Thr Ser Glu | 2-Naphthyl | Me | single bond | p-NA | TFMSA | SEQ ID NO:46 | 40.55 | 0.2512 | 161.4 |
| 2(51) | Gly Leu Ser Glu | 2-Naphthyl | Me | single bond | p-NA | TFMSA | SEQ ID NO:52 | 54.43 | 0.1631 | 333.8 |
| 2(53) | Gln Leu Ser Glu | 2-Naphthyl | Me | single bond | p-NA | TFMSA | SEQ ID NO:54 | 61.96 | 0.0998 | 621.0 |
| 2(54) | Lys Leu Ser Glu | 2-Naphthyl | Me | single bond | p-NA | TFMSA | SEQ ID NO:55 | 48.39 | 0.2739 | 176.7 |
| 2(56) | Ser Leu Ser Glu | 2-Naphthyl | Me | single bond | p-NA | TFMSA | SEQ ID NO:57 | 10.94 | 0.0194 | 562.6 |
| 2(57) | Thr Leu Ser Glu | 2-Naphthyl | Me | single bond | p-NA | TFMSA | SEQ ID NO:58 | 18.78 | 0.0284 | 660.9 |
| 2(61) | Ac Lys Asn Leu Ser Glu | 2-Naphthyl | Me | single bond | p-NA | TFMSA | SEQ ID NO:62 | 36.81 | 0.1681 | 219.0 |
| 2(63) | Pro Asn Asn Leu Ser Glu | 2-Naphthyl | Me | single bond | p-NA | TFMSA | SEQ ID NO:64 | 29.84 | 0.1763 | 169.2 |
| 2(69) | Me-Ala Leu Ser Glu | 2-Naphthyl | Me | single bond | p-NA | TFMSA | SEQ ID NO:70 | 73.08 | 0.9851 | 74.2 |
| 2(70) | Sar Leu Ser Glu | 2-Naphthyl | Me | single bond | p-NA | TFMSA | SEQ ID NO:71 | 49.56 | 0.3128 | 158.4 |
| 2(78) | Leu Ser Glu | 2-Naphthyl | Me | Leu | p-NA | TFMSA | SEQ ID NO:79 | 54.41 | 2.6240 | 20.74 |
| 2(80) | Leu Ser Glu | 2-Naphthyl | Me | Gly | p-NA | TFMSA | SEQ ID NO:81 | 15.77 | 0.1500 | 105.48 |
| 2(83) | Sar Leu Ser Glu | 2-Naphthyl | Me | Ala | m-ASD | TFMSA | SEQ ID NO:84 | 70.66 | 2.3660 | 29.87 |
| 2(84) | Sar Ser Gly | 2-Naphthyl | Me | Ala | DCHA | TFMSA | SEQ ID NO:85 | 33.07 | 0.2767 | 119.5 |

Sample

Purified human pepsinogen II

Method for Assay

Reagent solution I (0.25 ml) was added to sample (0.025 ml). After incubation of the mixture at 37° C. for 5 minutes, Reagent solution II (0.05 ml) was added thereto. After incubation of the mixture at 37° C. for 5 minutes, the increase in absorbance (Es) at 405 nm with reference at 480 nm was determined. On the other hand, reagent blank value (E(BL)) was determined by the same procedure as above using saline. According to the following, the increase in absorbance for 5 minutes (E) was calculated.

$$E=Es-E(BL)$$

The correlation between the concentration of pepsinogen II and increase in absorbance is shown in FIG. 1.

As is shown clearly from FIG. 1, calibration curve obtained from each pepsinogen II level (ng/ml) and the plotted increase in absorbance passes through zero point showing a good linearity and quantatativeness.

EXAMPLES 5

Assaying Human Pepsinogen II in Blood by the Method of the Present Invention (The Correlation of the Method Between the Present Invention and RIA)

Reagent Solutions I and II

Same solutions as Example 4.

Sample

52 Samples of human serum

Method for Assay

By the same procedure as Example 4, the increase in absorbance for 5 minutes (E) was calculated.

Comparison

The assaying serum pepsinogen II was carried out by a marketed kit for assaying pepsinogen II (Dinabott Co) (RIA method) according to the procedure described in explanation. The correlation of the results of the method between the present invention and RIA is shown in FIG. 2.

Figure 2:
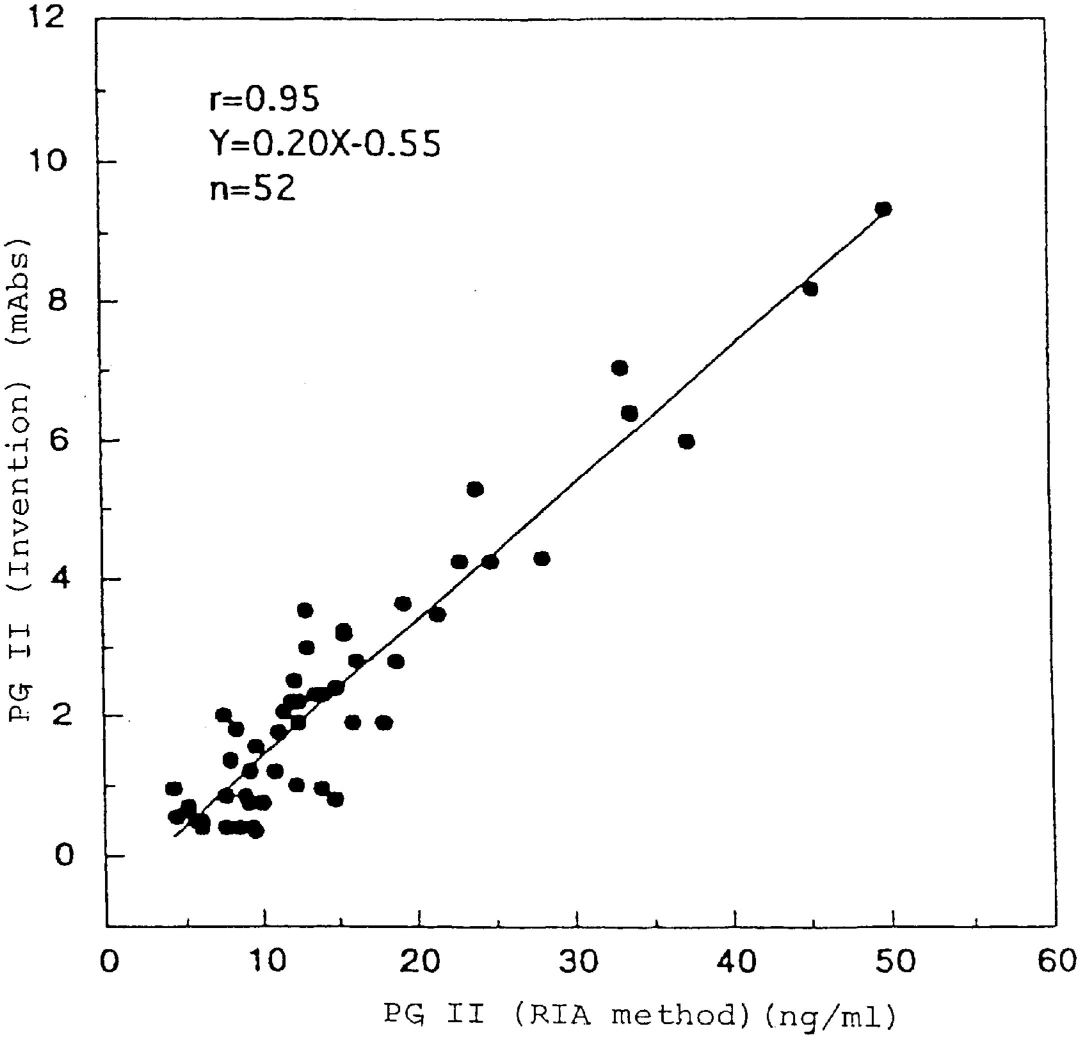
FIG. 2 shows correlation between a conventional method for assaying serum pepsinogen II (RIA) using a kit for assaying pepsinogen II (marketed from Dinabott Co), and a method for assaying of the present invention. The values on the abscissa and ordinate indicate the detected value (ng/ml) determined by RIA method and the increase of absorbance determined by the method of the present invention, respectively.

As is shown clearly from FIG. 2, we understand that there is a good correlation of the results of the method between the present invention and RIA, and that serum pepsinogen II was determined correctly by the method of the present invention.

EXAMPLE 6

Assaying Human Pepsinogen II by the Method of the Present Invention

Reagent Solution III

Nα-Me-GlySerGlyAla(2-Naph)AlaAla-DCHA.TFMSA (SEQ ID NO:85)(prepared in Example 2(84).) and N-ethyl-N-(3-sulphopropyl)-3-methyoxyaniline sodium salt.monohydrate (marketed from Dojin Chemical Research Institute Co.) were dissolved into citrate buffer (50 mM, pH2.0) to be at the concentration of 0.36 mM and 40 mM, respectively.

Reagent Solution IV

Aminopeptidase M (marketed from Beringer Co.) and polyphenoloxidase (marketed from Takara-shuzo) were dissolved into Tris-HCl buffer (2.0 M, pH8.33) to be at concentration of 0.67 U/ml and 0.2 U/ml, respectively.

Sample

Purified human pepsinogen II

Method for Assay

Reagent solution III (0.25 ml) was added to sample (0.025 ml). After incubation of the mixture at 37° C. for 5 minutes, Reagent solution IV (0.05 ml) was added thereto. After incubation of the mixture at 37° C. for 5 minutes, the increase in absorbance (Es) at 700 nm with reference at 800 nm was determined. On the other hand, reagent blank value (E(BL)) was determined by the same procedure as above using saline. The increase in absorbance for 5 minutes (E) was calculated by the same procedure as Example 4.

Figure 3:
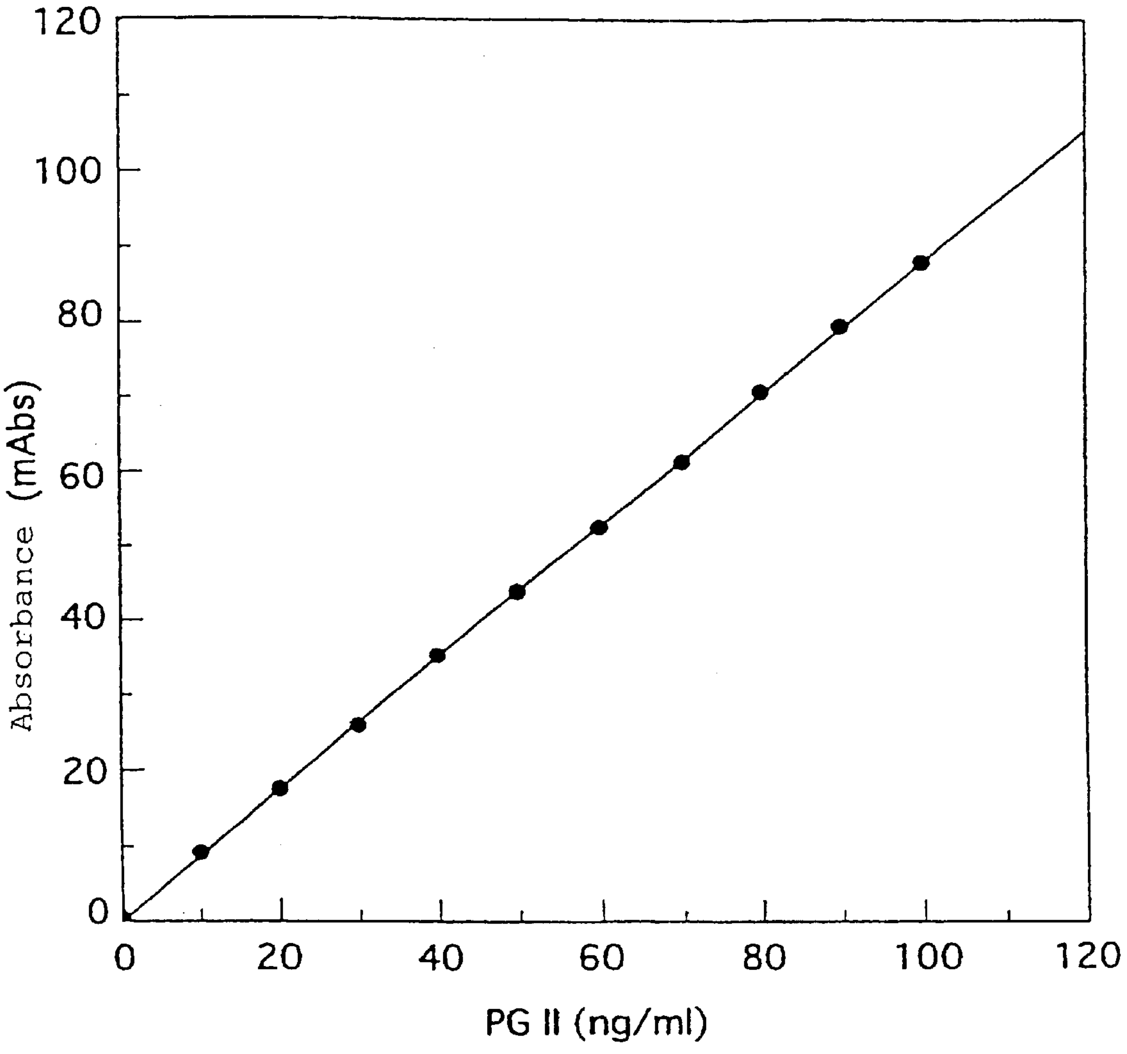
FIG. 3 shows calibration curve between pepsinogen II level (ng/ml) and the plotted increase of absorbance in Example 6.

The correlation between the concentration of pepsinogen II and increase in absorbance is shown in FIG. 3.

As is shown clearly from FIG. 3, calibration curve obtained from each pepsinogen II level (ng/ml) and the plotted increase in absorbance passes through zero point showing a good linearity and quantatativeness.

EXAMPLES 7

Assaying Human Pepsinogen II by the Method of the Present Invention (The Correlation of the Method Between the Present Invention and RIA)

Reagent Solutions III and IV

Same solution as Example 6.

Sample

52 Samples of human serum

Method for Assay

By the same procedure as Example 6, the increase in absorbance for 5 minutes (E) was calculated.

Comparison

The assaying serum pepsinogen II was carried out by the same procedure as Example 5. The correlation of the results of the method between the present invention and RIA is shown in FIG. 4.

Figure 4:
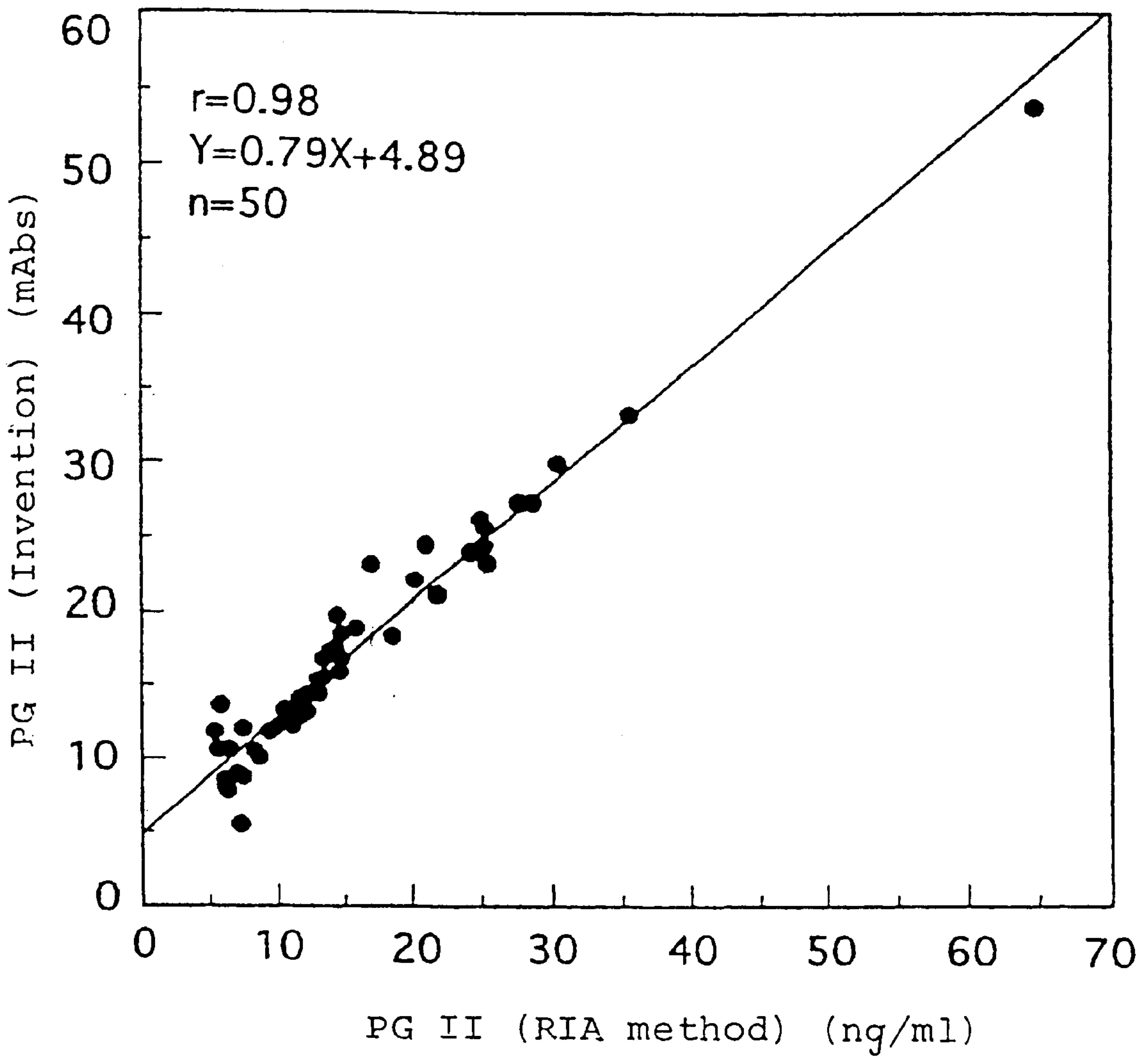
FIG. 4 shows correlation between a conventional method for assaying serum pepsinogen II (RIA) using a kit for assaying pepsinogen II (marketed from Dinabott Co), and a method for assaying of the present invention. The values on the abscissa and ordinate indicate the detected value (ng/ml) determined by RIA method and the increase of absorbance determined by the method of the present invention, respectively.

As is shown clearly from FIG. 4, we understand that there is a good correlation of the results of the method between the present invention and RIA, and that serum pepsinogen II was determined correctly by the method of the present invention.

What is claimed is:

1. A peptide of the formula (I)

(I)

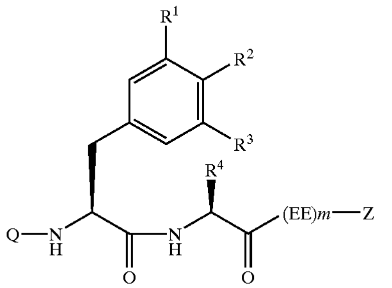

wherein,

Q is $Q^a$—(AA)n—, wherein AA is L-amino acid, n is 0 or an integer of 1–15, $Q^a$ is hydrogen, C1–4 alkyl, an amino-protective group, D- or L-amino acid residue or $NH_2$—$(CH_2)$r—CO—, where r is an integer of 2–7, $R^1$ and $R^2$ are (i) hydrogen or halogen or, (ii) $R^1$, $R^2$ and an unsaturated bond together form an aromatic carbon ring that may be substituted by halogen, $R^3$ is hydrogen or halogen, $R^4$ is hydrogen, C1–3 alkyl or hydroxymethyl, EE is D- or L-amino acid, m is 0 or 1, and Z is an aniline derivative residue, an aminocoumarine derivative residue or an aminonaphthalene derivative residue, with the proviso that (I) when n is 2 or more, each AA is same or different, and that (2) the compounds wherein all of $R^1$, $R^2$ and $R^3$ are hydrogen are excluded, or an acid addition salt thereof.

2. A peptide according to claim 1 in which m is 0.

3. A peptide according to claim 1 in which m is 1.

4. A peptide according to claims 1 to 3 in which Q is $Q^b$—(AA)s—$A^1$— wherein, $A^1$ is Gly, Ala, Ser, Asp, Glu, Asn, Gln or Met, s is an integer of 2, 3, 4 or 5, $Q^b$ is hydrogen, C1–4 alkyl, C 1–6 alkylcarbonyl, D- or L-amino acid or $NH_2$—$(CH_2)$r—CO—, where r is as defined in claim 1, and each AA is as defined in claim 1.

5. A peptide according to claims 1 to 3 in which Q is $Q^b$—(AA)t—$A^2$—$A^{11}$— wherein $A^{11}$ is Gly, Ala, Glu or Asn, $A^2$ is Gly, Ala, Leu, Ser, Asp, Glu, Asn or Gln, t is an integer of1, 2, 3 or 4, $Q^b$ is hydrogen, C1–4 alkyl, C1–6 alkylcarbonyl, D- or L-amino acid or $NH_2$—$(CH_2)$r—CO—, where r is as defined in claim 1, and each AA is as defined in claim 1.

6. A peptide according to claims 1 to 3 in which Q is $Q^b$—(AA)t—$A^{22}$—$A^{11}$— wherein $A^{11}$ is Gly, Ala, Glu or Asn, $A^{22}$ is Gly, Ser, Glu or Gln, t is an integer of1, 2, 3or 4, $Q^b$ is hydrogen, C1–4 alkyl, C 1–6 alkylcarbonyl, D- or L-amino acid or $NH_2$—$(CH_2)$r—CO— where r is as defined in claim 1, and each AA is as defined in claim 1.

7. A peptide of the formula (I-A):

(I-A)

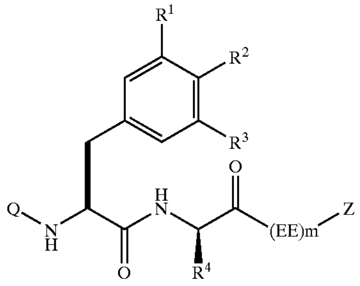

wherein, each symbol is as defined in Table 1 (Tables 1-1~1-4):

TABLE 1

Definition of each symbol

| No. | Q | 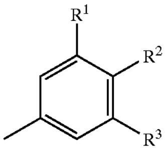 | $R^4$ | (EE)m | Z | SEQ ID NO: |
|---|---|---|---|---|---|---|
| (1) | Pro Leu Ser Glu | 2-Naphthyl | Me | single bond | p-NA | SEQ ID NO:1 |
| (2) | Leu Ser | 4-I-Phenyl | H | single bond | p-NA | SEQ ID NO:2 |
| (3) | Pro Gln Gln Ala | 2-Naphthyl | H | single bond | p-NA | SEQ ID NO:3 |
| (4) | Pro Gln Gln Ala | 4-I-Phenyl | H | single bond | p-NA | SEQ ID NO:4 |
| (5) | Pro Gln Gln Ala | 4-Cl-Phenyl | H | single bond | p-NA | SEQ ID NO:5 |
| (6) | Pro Gln Gln Ala | 2-Naphthyl | Me | single bond | p-NA | SEQ ID NO:6 |
| (7) | Pro Gln Gln Ala | 4-I-Phenyl | Me | single bond | p-NA | SEQ ID NO:7 |
| (8) | Pro Gln Gln Ala | 4-Cl-Phenyl | Me | single bond | p-NA | SEQ ID NO:8 |
| (9) | Pro Gln Gln Ala | 2-Naphthyl | Et | single bond | p-NA | SEQ ID NO:9 |
| (10) | Pro Gln Gln Ala | 4-I-Phenyl | Et | single bond | p-NA | SEQ ID NO:10 |
| (11) | Pro Gln Gln Ala | 4-Cl-Phenyl | Et | single bond | p-NA | SEQ ID NO:11 |
| (12) | Pro Gln Gln Ala | 2-Naphthyl | n-Pr | single bond | p-NA | SEQ ID NO:12 |
| (13) | Pro Gln Gln Ala | 4-I-Phenyl | n-Pr | single bond | p-NA | SEQ ID NO:13 |
| (14) | Pro Gln Gln Ala | 4-Cl-Phenyl | n-Pr | single bond | p-NA | SEQ ID NO:14 |
| (15) | Ac Lys Pro Gln Gln Ala | 4-I-Phenyl | Me | single bond | p-NA | SEQ ID NO:15 |
| (16) | Leu Pro Gln Gln Ala | 4-I-Phenyl | Me | single bond | p-NA | SEQ ID NO:16 |
| (17) | Asn Pro Gln Gln Ala | 4-I-Phenyl | Me | single bond | p-NA | SEQ ID NO:17 |
| (18) | Gln Pro Gln Gln Ala | 4-I-Phenyl | Me | single bond | p-NA | SEQ ID NO:18 |
| (19) | Ala Pro Gln Gln Ala | 4-I-Phenyl | Me | single bond | p-NA | SEQ ID NO:19 |
| (20) | Val Pro Gln Gln Ala | 4-I-Phenyl | Me | single bond | p-NA | SEQ ID NO:20 |
| (21) | Gly Pro Gln Gln Ala | 4-I-Phenyl | Me | single bond | p-NA | SEQ ID NO:21 |
| (22) | Phe Pro Gln Gln Ala | 4-I-Phenyl | Me | single bond | p-NA | SEQ ID NO:22 |
| (23) | Pro Gln Gln Asn | 2-Naphthyl | Me | single bond | p-NA | SEQ ID NO:23 |
| (24) | Pro Gln Gln Gln | 2-Naphthyl | Me | single bond | p-NA | SEQ ID NO:24 |
| (25) | Pro Gln Gln Gly | 2-Naphthyl | Me | single bond | p-NA | SEQ ID NO:25 |
| (26) | Pro Gln Gln Met | 2-Naphthyl | Me | single bond | p-NA | SEQ ID NO:26 |
| (27) | Pro Gln Gln Ser | 2-Naphthyl | Me | single bond | p-NA | SEQ ID NO:27 |
| (28) | Pro Gln Gln Asp | 2-Naphthyl | Me | single bond | p-NA | SEQ ID NO:28 |
| (29) | Pro Gln Gln Glu | 2-Naphthyl | Me | single bond | p-NA | SEQ ID NO:29 |
| (30) | Pro Gln Asn Glu | 2-Naphthyl | Me | single bond | p-NA | SEQ ID NO:30 |
| (31) | Pro Gln Ala Glu | 2-Naphthyl | Me | single bond | p-NA | SEQ ID NO:31 |
| (32) | Pro Gln Gly Glu | 2-Naphthyl | Me | single bond | p-NA | SEQ ID NO:32 |
| (33) | Pro Gln Leu Glu | 2-Naphthyl | Me | single bond | p-NA | SEQ ID NO:33 |
| (34) | Pro Gln Glu Glu | 2-Naphthyl | Me | single bond | p-NA | SEQ ID NO:34 |
| (35) | Pro Gln Asp Glu | 2-Naphthyl | Me | single bond | p-NA | SEQ ID NO:35 |
| (36) | Pro Gln Ser Glu | 2-Naphthyl | Me | single bond | p-NA | SEQ ID NO:36 |
| (37) | Pro Asn Ser Glu | 2-Naphthyl | Me | single bond | p-NA | SEQ ID NO:37 |
| (38) | Pro Ala Ser Glu | 2-Naphthyl | Me | single bond | p-NA | SEQ ID NO:38 |
| (39) | Pro Val Ser Glu | 2-Naphthyl | Me | single bond | p-NA | SEQ ID NO:39 |
| (40) | Pro Met Ser Glu | 2-Naphthyl | Me | single bond | p-NA | SEQ ID NO:40 |
| (41) | Pro Ile Ser Glu | 2-Naphthyl | Me | single bond | p-NA | SEQ ID NO:41 |
| (42) | Pro Gly Ser Glu | 2-Naphthyl | Me | single bond | p-NA | SEQ ID NO:42 |
| (43) | Pro Glu Ser Glu | 2-Naphthyl | Me | single bond | p-NA | SEQ ID NO:43 |
| (44) | Pro Asp Ser Glu | 2-Naphthyl | Me | single bond | p-NA | SEQ ID NO:44 |
| (45) | Pro Ser Ser Glu | 2-Naphthyl | Me | single bond | p-NA | SEQ ID NO:45 |
| (46) | Pro Thr Ser Glu | 2-Naphthyl | Me | single bond | p-NA | SEQ ID NO:46 |

TABLE 1-continued

Definition of each symbol

| No. | Q | 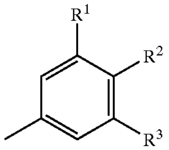 | R4 | (EE)m | Z | SEQ ID NO: |
|---|---|---|---|---|---|---|
| (47) | Asn Leu Ser Glu | 2-Naphthyl | Me | single bond | p-NA | SEQ ID NO:47 |
| (48) | Ala Leu Ser Glu | 2-Naphthyl | Me | single bond | p-NA | SEQ ID NO:48 |
| (49) | Val Leu Ser Glu | 2-Naphthyl | Me | single bond | p-NA | SEQ ID NO:49 |
| (50) | Met Leu Ser Glu | 2-Naphthyl | Me | single bond | p-NA | SEQ ID NO:50 |
| (51) | Ile Leu Ser Glu | 2-Naphthyl | Me | single bond | p-NA | SEQ ID NO:51 |
| (52) | Gly Leu Ser Glu | 2-Naphthyl | Me | single bond | p-NA | SEQ ID NO:52 |
| (53) | Leu Leu Ser Glu | 2-Naphthyl | Me | single bond | p-NA | SEQ ID NO:53 |
| (54) | Gln Leu Ser Glu | 2-Naphthyl | Me | single bond | p-NA | SEQ ID NO:54 |
| (55) | Lys Leu Ser Glu | 2-Naphthyl | Me | single bond | p-NA | SEQ ID NO:55 |
| (56) | Glu Leu Ser Glu | 2-Naphthyl | Me | single bond | p-NA | SEQ ID NO:56 |
| (57) | Ser Leu Ser Glu | 2-Naphthyl | Me | single bond | p-NA | SEQ ID NO:57 |
| (58) | Thr Leu Ser Glu | 2-Naphthyl | Me | single bond | p-NA | SEQ ID NO:58 |
| (59) | Tyr Leu Ser Glu | 2-Naphthyl | Me | single bond | p-NA | SEQ ID NO:59 |
| (60) | Ac Lys Leu Ser Glu | 2-Naphthyl | Me | single bond | p-NA | SEQ ID NO:60 |
| (61) | Pro Asn Leu Ser Glu | 2-Naphthyl | Me | single bond | p-NA | SEQ ID NO:61 |
| (62) | Ac Lys Asn Leu Ser Glu | 2-Naphthyl | Me | single bond | p-NA | SEQ ID NO:62 |
| (63) | Pro Ser Asn Leu Ser Glu | 2-Naphthyl | Me | single bond | p-NA | SEQ ID NO:63 |
| (64) | Pro Asn Asn Leu Ser Glu | 2-Naphthyl | Me | single bond | p-NA | SEQ ID NO:64 |
| (65) | Pro Gly Asn Leu Ser Glu | 2-Naphthyl | Me | single bond | p-NA | SEQ ID NO:65 |
| (66) | Ac Lys Ala Leu Ser Glu | 2-Naphthyl | Me | single bond | p-NA | SEQ ID NO:66 |
| (67) | β-Ala Asn Leu Ser Glu | 2-Naphthyl | Me | single bond | p-NA | SEQ ID NO:67 |
| (68) | Sar Asn Leu Ser Glu | 2-Naphthyl | Me | single bond | p-NA | SEQ ID NO:68 |
| (69) | Me-Val Leu Ser Glu | 2-Naphthyl | Me | single bond | p-NA | SEQ ID NO:69 |
| (70) | Me-Ala Leu Ser Glu | 2-Naphthyl | Me | single bond | p-NA | SEQ ID NO:70 |
| (71) | Sar Leu Ser Glu | 2-Naphthyl | Me | single bond | p-NA | SEQ ID NO:71 |
| (72) | Pro Leu Ser Glu | 4-Cl-Phenyl | Me | single bond | p-NA | SEQ ID NO:72 |
| (73) | Pro Leu Ser Glu | 3,4-DCP | Me | single bond | p-NA | SEQ ID NO:73 |
| (74) | Val Leu Ser Glu | 4-Cl-Phenyl | Me | single bond | p-NA | SEQ ID NO:74 |
| (75) | D-Ala Asn Leu Ser Glu | 2-Naphthyl | Me | single bond | p-NA | SEQ ID NO:75 |
| (76) | D-Ala Leu Ser Glu | 2-Naphthyl | Me | single bond | p-NA | SEQ ID NO:76 |
| (77) | β-Ala Leu Ser Glu | 2-Naphthyl | Me | single bond | p-NA | SEQ ID NO:77 |
| (78) | γ-Abu Leu Ser Glu | 2-Naphthyl | Me | single bond | p-NA | SEQ ID NO:78 |
| (79) | Leu Ser Glu | 2-Naphthyl | Me | Leu | p-NA | SEQ ID NO:79 |
| (80) | Leu Ser Glu | 2-Naphthyl | Me | Ala | p-NA | SEQ ID NO:80 |
| (81) | Leu Ser Glu | 2-Naphthyl | Me | Gly | p-NA | SEQ ID NO:81 |
| (82) | Sar Leu Ser Glu | 2-Naphthyl | Me | Ala | p-NA | SEQ ID NO:82 |
| (83) | Sar Leu Ser Glu | 2-Naphthyl | Me | Gly | p-NA | SEQ ID NO:83 |
| (84) | Sar Leu Ser Glu | 2-Naphthyl | Me | Ala | m-ASD | SEQ ID NO:84 |
| (85) | Sar Ser Gly | 2-Naphthyl | Me | Ala | DCHA | SEQ ID NO:85 |

in Table 1, the meaning of each abbreveated symbol is as follows:

Me=methyl,

Et=ethyl, n-Pr=n-propyl,

Ac=acetyl,

Sar=$N^{\alpha}$-methyl-glycine,

Me-Val=$N^{\alpha}$-methyl-valine,

Me-Ala=$N^{\alpha}$-methyl-alanine,

γ-Abu=γ-aminobutanoic acid, p-NA=p-nitroaniline residue, 3,4-DCP=3,4-dichlorophenyl, m-ASD=m-anisidine residue, DCHA=3,5-dichloro-4-hydroxyaniline residue.

8. A method for assaying human pepsinogen II or human pepsin II characterized by digesting a peptide of the formula (I) depicted in claim 1, wherein all the symbols are as defined in claim 1, or an acid addition salt thereof, by human pepsin II which is obtained by activation of human pepsinogen II in a sample or human pepsin II in a sample to obtain an amino acid derivative of the formula (II)

(II)

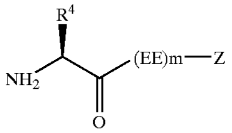

wherein all the symbols are as defined in claim 1, digesting the obtained amino acid derivative of the formula (II) by aminopeptidase to obtain an aniline, aminocoumarine or aminonaphthalene derivative of the formula Z—H, and then detecting the obtained aniline, aminocoumarine or aminonaphthalene derivative.

9. A method for assaying according to claim 8 using a peptide of the formula (I-A) depicted in claim 7 (wherein all the symbols are as defined in claim 7) or an acid addition salt thereof.

10. A kit for assaying human pepsinogen II or human pepsin II which is characterized by comprising a peptide of the formula (I) as depicted in claim 1 (wherein all the symbols are as defined in claim 1) or an acid addition salt thereof as a substrate and aminopeptidase.

11. A peptide according to claim 1, wherein m+n is an integer of 1 or more.

* * * * *